(12) United States Patent
Yerxa et al.

(10) Patent No.: US 6,624,150 B2
(45) Date of Patent: Sep. 23, 2003

(54) METHOD OF TREATING GASTROINTESTINAL TRACT DISEASE WITH PURINERGIC RECEPTOR AGONISTS

(75) Inventors: Benjamin R. Yerxa, Raleigh, NC (US); Janet L. Rideout, Raleigh, NC (US); William Pendergast, Durham, NC (US); Sammy Ray Shaver, Chapel Hill, NC (US); Zhen Zhang, Apex, NC (US); Ward M. Peterson, Durham, NC (US); Matthew Cowlen, Chapel Hill, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 254 days.

(21) Appl. No.: 09/747,777

(22) Filed: Dec. 22, 2000

(65) Prior Publication Data

US 2002/0052336 A1 May 2, 2002

Related U.S. Application Data

(63) Continuation-in-part of application No. 09/512,867, filed on Feb. 25, 2000, now Pat. No. 6,331,529.
(60) Provisional application No. 60/171,710, filed on Dec. 22, 1999, and provisional application No. 60/121,754, filed on Feb. 26, 1999.

(51) Int. Cl.[7] ............................................... A61K 31/70
(52) U.S. Cl. ........................................... 514/47; 514/51
(58) Field of Search ....................................... 514/47, 51

(56) References Cited

FOREIGN PATENT DOCUMENTS

| WO | WO 95/10287 | 4/1995 |
|---|---|---|
| WO | WO 00/50024 | 8/2000 |

OTHER PUBLICATIONS

International Search Report, Feb. 4, 2002.
Ota, et al. "$P_2$ Purinergic Receptor Regulation of Mucus Glycoprotein Secretion by Rabbit Gastric Mucous Cells in a Primary Culture," *Gastroenterology* 106:1485–1492 (1994).
Roman, et al., "Emerging roles of Purinergic Signaling in Gastrointestinal Epithelial Secretion and Hetatobiliary Function," *Gastroenterology* 116(4):964–979 (1999).

*Primary Examiner*—Zohreh Fay
(74) *Attorney, Agent, or Firm*—Albert P. Halluin; Viola T. Kung; Howrey, Simon, Arnold & White, LLP

(57) ABSTRACT

The invention provides a method of regulating water and mucin secretions and fluid transport in the gastrointestinal tract. The invention also provides a method for treating a gastrointestinal disease in which the mucosal barrier of the gastrointestinal system is impaired. The invention additionally provides a method for correcting disorders of fluid secretion or absorption in the gastrointestinal system. The method comprises administering to a patient a pharmaceutical composition comprising a purinergic P2Y receptor agonist, in an amount effective to regulate water and mucin secretions or to correct abnormal fluid transport in the gastrointestinal tract. The pharmaceutical composition used in this invention comprises a P2Y purinergic receptor agonist such as uridine 5'-diphosphate (UDP), uridine 5'-triphosphate (UTP), cytidine 5'-diphosphate (CDP), cytidine 5'-triphosphate (CTP), adenosine 5'-diphosphate (ADP), adenosine 5'-triphosphate (ATP), and their analogs; and dinucleotide polyphosphate compounds of general Formula (IV). Said compound is prepared in an oral form, an injectable form, or a suppository form, and administered to a patient.

13 Claims, 10 Drawing Sheets

(4 of 10 Drawing Sheet(s) Filed in Color)

METHOD OF TREATING GASTROINTESTINAL TRACT DISEASE WITH PURINERGIC RECEPTOR AGONISTS

This application is a continuation in part of 09/512,867, filed Feb. 25, 2000 now U.S. Pat. No. 6,331,529 and claims priority to U.S. Provisional 60/171,710 filed Dec. 22, 1999, and 60/121,754, filed Feb. 26, 1999, which is hereby incorporated herein in its entirety by reference.

TECHNICAL FIELD

This invention relates to a method of regulating mucus secretions and fluid transport in the gastrointestinal system of a patient by administering purinergic receptor agonists such as certain uridine, adenine, or cytidine 5'-di- and triphosphates, dinucleoside polyphosphates and their analogs thereof.

BACKGROUND OF THE INVENTION

There are many situations where it is therapeutically desirable to increase the amount of mucin secretion, bicarbonate secretions, and/or degree of hydration in gastrointestinal systems. The gastrointestinal system operates principally to extract energy and metabolic building blocks from the nutrient materials presented to it. The digestive tract includes the buccal cavity (primary salivary glands), esophagus, stomach, small intestine, large intestine, rectum, and ancillary organs (pancreas, liver and gall bladder). When the mucosal barrier is impaired in the digestive tract, it results in diseases such as dry mouth, gastro-esophageal reflux disease, peptic ulcer, inflammatory bowel disease, etc. Abnormal fluid and electrolytic transport in the lower gastrointestinal tract results in disorders such as constipation and diarrhea.

Mucus is a viscous material that coats many epithelial surfaces and is secreted into fluids such as saliva. It is composed chiefly of mucins and inorganic salts suspended in water. Mucus adheres to many epithelial surfaces, where it serves as a diffusion barrier against contact with noxious substances (e.g. gastric acid, digestive enzymes and bacteria) and as a lubricant to minimize shear stresses. Such mucous coatings are particularly prominent on the epithelia of the gastrointestinal, respiratory and genital tracts. Mucous is also an abundant and important component of saliva, giving it virtually unparalleled lubricating properties. Mucus-secreting cells such as goblet cells are abundant in the epithelium of the gastrointestinal tracts. Numerous submucosal mucous glands are scattered along the esophagus and especially accumulated below the upper and above the lower esophageal sphincters. Many of the acinar epithelial cells in salivary glands secrete mucus. The major structural molecules of the mucus layer are mucins, which are a family of large, heavily glycosylated proteins. The dense "sugar coating" of mucins gives them considerable water-holding capacity and makes them resistant to proteolysis, which may be important in maintaining mucosal barriers.

Bicarbonate secretion plays an important role in the maintenance of mucosal health in the gastrointestinal tract. The production of bicarbonate and mucus by the esophagus in response to local acidification provides an inherent mechanism for resisting acid-induced damage. The secretion of salivary protective factors, including bicarbonate, as well as bicarbonate secreted from esophageal submucosal glands, are important in preventing esophageal mucosal injury associated with gastrointestinal reflux disease. Mucosal bicarbonate also provides an important mechanism for protection against acid damage in the proximal duodenum, in which adherent mucus provides a stable protective layer supporting surface neutralization of acid by mucosal bicarbonate. [Nucleotides stimulate bicarbonate secretion in guinea pig pancreatic duct (Ishiguro el al 1999, J. Physiol. 519 Pt 2:551–558) and CFTR knockout mouse gall bladder epithelium (Clarke et al. 2000, Am. J Physiol. Gastrointest. Liver Physiol. 279:G132–138)].

Proper regulation of fluid and electrolytic absorption and secretion at appropriate regions along the gastrointestinal system is required for normal digestive function. Impairment of fluid transport leads to a variety of disorders, including constipation and diarrhea. Constipation is associated with a delay in the transit of fecal matter through the large intestine. The increased resident time of feces in the large intestine leads to increased fluid absorption by the colonic epithelium, and results in dehydration of feces and the subsequent production of dry, hard feces in the descending colon. Conversely, diarrhea results from rapid movement of fecal matter through the large intestine, resulting from either increased fluid secretion in the small intestine or by reduced fluid absorption in the colon.

Xerostomia, commonly known as dry mouth, results from the underproduction of saliva. Dry mouth is caused by radiation treatment or diseases that damage salivary glands and decrease salivary flow. Gastroesophageal reflux disease is the condition where the degree of exposure of esophageal mucosa to gastric contents is greater than normal. The most common manifestation is heartburn. Pharmacological treatment involves the use of H2 antagonists (e.g., Tagamet®, Zantac®, Pepcid®, Axid®) and proton pump inhibitors such as Prilosec® or Prevacid®, for treatment of acute disease. Peptic ulcer diseases include gastric ulcer, pyloric channel ulcer and duodenal ulcer. Ulceration results from a complex interplay of acid and chronic inflammation induced by *Helicobacter pylori* infection. Patients with duodenal ulcers have high acid secretion. Increased acid secretion causes changes in the wall of the duodenum, setting the stage for invasion by *H. pylori*. Drugs for treating peptic ulcer diseases include Histamine-2 (H2) blockers (Tagamet®, Zantac®, Axid®, Pepcid®, etc.), sucralfate, proton pump inhibitors, and antacids. Inflammatory bowel disease is classified into two types: ulcerative colitis and Crohn's disease. Ulcerative colitis affects the colon/rectum and involves the mucosa or the innermost lining of the colon wall. Crohn's disease is a transmural disease involving all layers of the bowel and may involve any part of the gut, from mouth to anus. Medical treatment of inflammatory bowel disease includes aminosalicylates and corticosteroids. Corticosteroids have substantial long-term toxicity. As an alternative to conventional therapies, medical researchers have sought to develop new treatments for gastrointestinal diseases.

The following references disclose the role of mucus integrity and mucin secretion in some diseases of the gastrointestinal tract. Rhodes et al. (*Gut*, 26:1312–1318 (1985)) suggested that colonic mucus undergoes continual desulphation and desialation in vivo as a result of faecal enzyme activity; altered susceptibility of colonic mucus may be important in the pathogenesis of colonic disease. Somasundaram et al. (*Clin. Exp. Pharmacol. Physiol.*, 14:309–318 (1987)) report that the integrity of the gastric mucosa and its ability to secrete mucus are essential for protection of gastric mucosa against ulceration induced by aggressive factors active in any stress situation. Desai et al. (*J. Pharm. Pharmacol.* 47:734–738 (1995)) showed that SKF 38393, a specific dopamine D1-receptor agonist, was effective in preventing gastric and duodenal ulceration in rats. Sarosiek et al. (Digestion, 56 Suppl. 1 :15–23 (1995)) reported that the rate of secretion of esophageal mucin, EGF and PGE2, under the impact of HC1/pepsin in patients with reflux esophagitis, was significantly impaired. Saitoh et al. (*Dig. Dis. Sci.* 41:1768–1774 (1996)) showed that compared with healthy subjects, the total yields of mucin from ulcerative colitis patients were low due to a deficiency of neutral mucin, whereas those from Crohn's disease patients were high due to high-molecular weight mucin. Sarosiek et al. (*Gastroenterology*, 10:675–681 (1996)) suggest that an increase in the secretion rate of inorganic and organic protective components in saliva may be useful to the treatment of gastroesophageal reflux disease. Zeeh (*Gastroenterology*, 110:1 077–1083 (1996)) reported that administration of keratinocyte growth factor ameliorates mucosal injury in an experimental model of colitis in rats. Abbas et al. (*Indian J Exp. Biol.* 36:182–186 (1998)) report that the antiulcerogenic effect of GABA and baclofen may be due to their predominant effects on mucosal defensive factors like enhanced mucin secretion and decreased cell shedding or mucosal damage. Nath et al. (*Clin. Exp. Pharmacol. Physiol.* 25:564–567 (1998)) report that polyriboinosinic-polyribocytidylic acid had a potent antigastric ulcer effect on rats; polyriboinosinic-polyribocytidylic acid was shown to cause a decrease in free and total acid and pepsin and an increase in mucin content in Shay rat. Newton et al. (*Gut*, 43:470–475 (1998)) report that *H. pylori* in vivo causes structural changes in the adherent gastric mucus layer but the mucus barrier thickness is not compromised.

The following references disclose the compositions of purinergic receptor agonists and/or treatment of diseases. Uridine 5'-triphosphate has been shown to increase both the rate and total amount of mucin secretion by Goblet cells in vitro (Lethem et al., *Am. J. Respir. Cell Mol. Biol.,* 9:315–322 (1993)). U.S. Pat. No. 5,900,407 (Yerxa et al.) discloses a method for the stimulation of tear secretion in a subject in need of treatment. The method comprises administering to the ocular surfaces of the subject a purinergic receptor agonist such as uridine 5'-triphosphate, cytidine 5'-triphosphate, adenosine 5'-triphosphate, or their analogs and derivatives, in an amount effective to stimulate tear fluid secretion. U.S. Pat. No. 5,837,861 (Pendergast et al.) discloses P2Y$_2$ purinergic receptors of dinucleoside polyphosphates having structure of Formula I, wherein X is oxygen, methylene, or difluoromethylene; n=0 or 1; m=0 or 1; n+m=0, 1 or 2; and B and B' are each independently a purine residue or a pyrimidine residue linked through the 9- or 1-position. The compounds are useful in the treatment of chronic obstructive pulmonary diseases, bronchitis, certain pneumonias, cystic fibrosis, sinusitis, and otitis media. U.S. Pat. No. 5,763,447 (Jacobus et al.) discloses a method of promoting drainage of mucous secretions in the congested airway of an immobilized patient. The method comprises administering to the airway of the patient a uridine phosphate such as uridine 5'-triphosphate (UTP), or P,$^1$P$^4$ -di(uridine-5')tetraphosphate, in an amount effective to promote drainage of fluid in the congested airway, including sinuses, by hydrating mucous secretions or by stimulating ciliary beat frequency in the airway. U.S. Pat. Nos. 5,789,391, 5,981,506, 5,972,904 and 5,958,897 are directed to a method of promoting drainage of congested mucous secretions in the sinuses of a subject in need. The method comprises administering to the sinuses of the subject a uridine phosphate such as uridine 5'-triphosphate (UTP) or P$^1$, P$^4$-di(uridine-5') tetraphosphate, an analog of UTP, or any other analog, in an amount effective to promote drainage of congested fluid in the sinuses by hydrating mucous secretions or by stimulating ciliary beat frequency in the sinuses. U.S. Pat. No. 5,968,913 is directed to a pharmaceutical compositions of UTP for use in promoting increased mucociliary clearance of retained mucous secretions of the human airways, middle/inner ears or sinuses. U.S. Pat. No. 5,763,447 is directed to a method of preventing or treating pneumonia, including ventilator-associated pneumonia, in a bedridden or immobilized subject in need of such treatment. The method comprises administering to the airways of the patient a uridine phosphate such as uridine 5'-triphosphate (UTP), P$^1$, P$^4$ -di(uridine-5')tetraphosphate, or their analogs, in an amount effective to promote drainage of fluid in the congested airways. WO 99/09998 discloses a method of using uridine 5'-diphosphate and analogs thereof to treat lung disease. The compounds described in the above references ('391, '506, '904, '897, '913 and '447 Patent and WO 99/09998), which have purinergic receptor activity, are incorporated herein by reference. U.S. Pat. No. 5,733,916 (Neely) discloses a method of preventing or treating ischemia-reperfusion injury or endotoxin-related lung injury by administration of a composition containing a selective Al adenosine receptor antagonist and/or a P$_2$X purinoceptor antagonist. Somers et al. (*Laboratory Investigation*, 78:1375–1383 (1998)) report that P2Y$_6$ receptor was highly expressed in the T cells infiltrating active inflammatory bowel disease, whereas P2Y$_6$ expression was absent from the T cells of unaffected bowel. Boyer et al., (Br. J. Pharmacol. 118:1959 (1996)) synthesized and tested a series of chain-extended 2-thioether derivatives of adenosine monophosphate (AMP) as agonists for activation of the phospholipase C-linked P2Y-purinoceptor of turkey erythrocyte membranes, the adenylyl cyclase-linked P2Y-purinoceptor of C6 rat glioma cells, and the cloned human P2U-receptor stably expressed in 1321N1 human astrocytoma cells.

Specific dinucleoside phosphate compounds known in other prior art are listed in Table I, along with their corresponding references. These compounds have not been used in the prior art to increase the mucus secretion or to correct for fluid and electrolytic imbalance in the gastrointestinal tract, and Applicants intend to include them in this invention.

TABLE I

| DINUCLEOSIDE PHOSPHATE COMPOUNDS IN THE LITERATURE | | | | | |
|---|---|---|---|---|---|
| Np$_2$N | Np$_2$N' | Np$_3$N | Np$_3$N' | Np$_4$N | Np$_4$N' |
| Ap$_2$A | Ap$_2$NAD | Up$_3$U | Ap$_3$T | Up$_4$U | Ap$_4$U |
| Gp$_2$G | Ap$_2$TAD | Ap$_3$A | m$^7$Gp$_3$G | Ap$_4$A | Ap$_4$C |
| m$^7$Gp$_2$m$^7$G | Ap$_2$C-NAD | Xp$_3$X | m$^{2,2,7}$Gp$_3$G | Cp$_4$C | Ap$_4$G |
| Up$_2$U | Ap$_2$C-PAD | m$^7$Gp$_3$m$^7$G | m$^{2,7}$Gp$_3$G | Gp$_4$G | Gp$_4$U |

TABLE I-continued

DINUCLEOSIDE PHOSPHATE COMPOUNDS IN THE LITERATURE

| | | | | | |
|---|---|---|---|---|---|
| (5-BrU)p$_2$(5-BrU) | Ap$_2$BAD | Gp$_3$G | Ap$_3$U | Xp$_4$X | Gp$_4$C |
| (AZT)p$_2$(AZT) | m$^7$Gp$_2$G | (5-BrU)p$_3$3(5-BrU) | Ap$_3$(5-BrU) | Dp$_4$D | Up$_4$C |
| (5-FU)p$_2$(5-FU) | Ap$_2$G | Cp$_3$C | Up$_3$(5-BrU) | eAp$_4$eA | Ap$_4$T |
| Ip$_2$I | Ap$_2$U | Ip$_3$I | Gp$_3$A | m$^7$Gp$_4$m$^7$G | m$^7$Gp$_4$G |
| | Ap$_2$(5-BrU) | Ap-CH$_2$-ppA | Gp$_3$C | (5-BrU)p$_4$(5-BrU) | m$^{2,7}$Gp$_4$G |
| | Up$_2$(5-BrU) | Ap-CF$_2$-ppA | Gp$_3$Gm | dAp$_4$dA | m$^{2,2,7}$Gp$_4$G |
| | (AZT)p$_2$(5-FU) | | Gp$_3$Am | 3'-dAp$_4$3'-dA | (5-BrU)p$_4$A |
| | Ap$_2$T | | m$^7$Gp$_3$m$^6$Am | dGp$_4$dG | (5-BrU)p$_4$U |
| | Gp$_2$A | | m$^7$Gp$_3$Gm | ApCH$_2$p$_3$A | Ap$_4$(8-BrA) |
| | Ip$_2$A | | Ap$_3$C | Ip$_4$I | Ap$_4$X |
| | 2dGp$_2$A | | Ap$_3$G | Ap$_2$CH$_2$p$_2$A | Ap$_4$I |
| | Ap$_2$C | | m$^7$Gp$_3$A | Ap$_2$CF$_2$p$_2$A | Ap$_4$dA |
| | | | Ip$_3$A | Dp$_2$CH$_2$p$_2$D | Ap$_4$d(5-FU) |
| | | | Ip$_3$G | Dp$_2$CF$_2$p$_2$D | Ap$_4$araA |
| | | | 2'dGp$_3$A | | Ap$_2$CH$_2$p$_2$U |
| | | | 2'dGp$_3$-2'dG | | Ap$_2$CH$_2$p$_2$G |
| | | | m$^7$Gp$_3$Am | | Ap$_3$CH$_2$pT |
| | | | Gp$_3$U | | ahaAp$_4$A |
| | | | m$^7$Gp$_3$Cm | | ahaAp$_4$G |
| | | | m$^7$Gp$_3$Um | | |
| | | | m$^7$Gp$_3$G | | |
| | | | App-CH$_2$-pT | | |
| | | | Ap-CF$_2$-ppA | | |

| Np$_5$N | Np$_5$N' | Np$_6$N | Np$_6$N' |
|---|---|---|---|
| Ap$_5$A | Ap$_5$T | Ap$_6$A | Ap$_6$T |
| Up$_5$U | Ap$_5$U | Up$_6$U | Ap$_6$U |
| (5-BrU)p$_5$(5-BrU) | Ap$_5$(5-BrU) | (5-BrU)p$_6$(5-BrU) | Up$_6$(5-BrU) |
| Gp$_5$G | Up$_5$(5-BrU) | Gp$_6$G | Ap$_6$(5-BrU) |
| 2'dGp$_5$2'dG | | | |
| Ip$_5$I | | | |

A = Adenosine
U = Uridine
G = Guanosine
T = Thymidine
X = Xanthosine
TAD = Tiazofurin
BAD = Benzamide riboside
D = 2,6-Diaminopurine
Gm = 2'-O-methylguanosine
Um = 2'-O-methyluridine
Cm = 2'-O-methylcytidine
X = Xanthosine
5-BrU = 5-bromouridine eA = Ethenoadenosine
m$^7$G = 7-Methylguanosine
m$^{2,7}$G = 2,7-Dimethylguanosine
m$^{2,2,7}$G = 2,2,7-Trimethylguanosine
NAD = nicotinamide riboside
C-NAD = C-nicotinamide riboside
C-PAD = C-picolinamide riboside
N = Nucleoside
Am = 2'-O-methyladenosine
m6Am = N6-methyl-2'-O-methyladenosine
aha = 8-(6-aminohexyl)
AZT =Thymine-3'-azido2',3'-dideoxy-D-riboside
5-FU = 5-fluorouridine (1) M. A. G. Sillero et al., Eur. J. Biochem., 76, 331 (1977)
(2) C. G. Vallejo et al., Biochim. Biophys. Acta, 483, 304 (1976)
(3) H. Coste et al., J. Biol. Chem., 262, 12096 (1987)
(4) K. E. Ng et al., Nucleic Acid Res., 15, 3573 (1987)
(5) J. Stepinski et al., Nucleosides & Nucleotides, 14, 717 (1995)
(6) A. Zatorski et el., J. Med. Chem., 39, 2422 (1996)
(7) P. Rotilan et al., FEBS, 280, 371 (1991)
(8) P. C. Zamecnik et al., Proc. Natl. Acad. Sci., 89, 2370 (1992)
(9) J. Walker et al., Biochemistry, 32, 14009 (1993)
(10) R. H. Hiderman et al., J. Biol. Chem., 266, 6915 (1991)
(11) J. Luthje et al., Eur. J. Biochem., 173, 241 (1988)
(12) R. H. Silverman et al., Microbiological Rev., 43, 27 (1979)
(13) C. D. Lobaton et al., Eur. J. Biochem., 50, 495 (1975)
(14) G. Lowe et al., Nucleosides & Nucleotides, 10, 181 (1991)
(15) G. M. Blackburn et al., Nucleosides & Nucleotides, 10, 549 (1991)
(16) J. C. Baker et al., Mutation Res., 208, 87 (1988)
(17) G. Klein et al., Biochemistry, 27, 1897 (1988)
(18) E. Castro et al., Br. J. Pharmacol., 100, 360 (1990)
(19) D. R. Elmaleh et al., Proc. Natl. Acad. Sci., 81, 918 (1984)
(20) R. Bone et al., J. Biol. Chem., 261, 16410 (1986)
(21) Fed. Amer. Soc. Exper. Bio., Abstr. Part I, no. 1878 (1991)
(22) M. T. Miras-Portugal et al., Ann. NY Acad. Sci., 603, 523 (1990)
(23) A. Guranowski et al., Biochemistry, 27, 2959 (1988)
(24) F. Grummt et al., Plant Mol. Bio., 2, 41 (1983)
(25) A. G. McLennan et al., Nucleic Acid Res., 12, 1609 (1984)
(26) P. Zamecnik et al., Analytical Biochem., 134, 1 (1983)
(27) E. Rapaport et al., Proc. Natl. Acad. Sci., 78, 838 (1981)
(28) T. Kimura et al., Biol. Pharm. Bull., 18, 1556 (1995)
(29) E. Schulze-Lohoff et al., Hypertension, 26, 899 (1995)
(30) B. K. Kim et al., Proc. Natl. Acad. Sci., 89, 11056 (1992)
(31) P. C. Zamecnik et al., Proc. Natl. Acad. Sci., 89, 2370 (1992)
(32) H. Morii et al., Eur. J. Biochem., 205, 979 (1992)
(33) E. Castro et al., Pflugers Arch., 426, 524 (1994)
(34) H. Schluter et al., Nature, 367, 186 (1994)
(35) E. Castro et al., Br. J. Pharmacol., 206, 833 (1992)
(36) T. Casillas et al., Biochemistry, 32, 14203 (1993)

(37) J. Pintor et al., J. Neurochem., 64, 670 (1995)
(38) E. Castro et al., J. Biol. Chem., 270, 5098 (1995)
(39) V. A. Panchenko et al., Neuroscience, 70, 353 (1996)
(40) E. Castro et al., Br. J. Pharmacol., 100, 360 (1990)
(41) J. Pintor et al., Gen. Pharmac., 26, 229 (1995)
(42) J. Pintor et al., Br. J. Pharmacol., 115, 895 (1995)
(43) A. Kanavarioti et al., Tett. Lett., 32, 6065 (1991)
(44) Stutts, M. J., III, et al., WO 96/40059
(45) Theoclitou, et al., *J. Chem. Soc. Perkin Trans I*, 2009–2019 (1996)
(46) Guranowski, A., et al. *Nucleosides and Nucleotides*, 14, 731–734 (1995)
(47) DeFlora, A., et al. WO 96/02554A1
(48) Visscher, J. et al. *Nucleic Acids Research*, 20, 5749–5752 (1992)
(49) Holler, E.; Holmquist, B, et al. *Biochemistry*, 22, 4924–4933 (1983)
(50) Orr, R. M.; et al. *Biochem. Pharmacol.* 673–677 (1988)
(51) Plateau, P., Fromant, et al. *Biochemistry*, 24, 914–922 (1985)
(52) Hagmeier, E., et al. *Journal of Chromatography*, 237, 174–177 (1982)
(53) Scheffzek, K, et al. *Biochemistry*, 35, 9716–9727 (1996)
(54) Stridh, S., et al. *Antiviral Research*, 97–105 (1981)
(55) Tarusova, N. B., et al. *Zh. Org. Khim.*, 24(7), 1474–1480 (Russian); through *Chem. Abs.* 110:154770 (1988)
(56) Hata, T., et al. *Chem. Lett.*, 987–990 (1976)
(57) Huhn, G. F., et al. *Separation Science and Technology*, 28, 1959–1970 (1993)
(58) Tumanov, Yu. V., et al. *Bioorg. Khim.*, 13, 921–927 (Russian); through *Chem Abs.*, 109:6867d (1987)
(59) Devash, Y. U.S. Pat. No. 4,855,304
(60) Pintor, J., et al. *Molecular Pharmacology* 51, 277–284 (1997)
(61) Stutts et al. U.S. Pat. No. 5,635,160.
(62) Thiermermann, C., et al. WO 98/55494
(63) Zamechik, P. C., et al. U.S. Pat. No. 5,049,550
(64) Pankiewicz, K. W., et al. WO98/15563
(65) Kim, B. K., et al. U.S. Pat. No. 5,681,823
(66) Stutts, et al., U.S. Pat. No. 5,935,555

P2Y purinergic receptors are purine and pyrimidine nucleotide receptors that couple to G proteins; they are 308 to 377 amino acid proteins with molecular weights of 41 to 53 kDa after glycosylation. P2Y receptors such as $P2Y_1$, $P2Y_2$ and $P2Y_6$ receptors are present in the gastrointestinal tract (Ralevic et al., Pharm. Rev. 50:415–492 (1998)). Because of the demonstrated ability of purinergic receptor agonists to stimulate mucus/mucin secretion in and around the eye (U.S. Pat. No. 5,900,407), and in lung and sinuses (U.S. Pat. No. 5,837,861), Applicants were motivated to investigate whether P2Y purinergic receptor ligands could affect mucus and/or mucin secretion, and to correct abnormal fluid transport in the gastrointestinal tract, and thus be effective in treating diseases and disorders of the upper and lower gastrointestinal tract.

Applicants have discovered that all P2Y receptors, including $P2Y_4$ and $P2Y_{11}$ are present in gastrointestinal tissues. Applicants also discover that mucus and mucin secretion, bicarbonate secretion and fluid transport in these tissues can be regulated via P2Y purinergic receptor-mediated mechanisms. P2Y purinergic receptor ligands, administered orally or systemically, provide a novel method of treating gastrointestinal disorders.

SUMMARY OF THE INVENTION

The invention provides a method of regulating mucus/mucin secretions, and fluid transport in the gastrointestinal tract. The invention provides a method for treating gastrointestinal disease in which the mucosal barrier of the gastrointestinal system is impaired. The invention additionally provides a method for correcting disorders of fluid secretion or absorption in the gastrointestinal tract resulting in either diarrhea or constipation. The method comprises administering to a patient a pharmaceutical composition comprising a purinergic P2Y receptor ligand, in an amount effective to regulate mucus/mucin and bicarbonate secretions and fluid transport in the gastrointestinal tract. Methods of administering include oral and systemic administration. The diseases treated include diseases and disorders of the buccal cavity, esophagus, stomach, small intestine, large intestine, rectum, and ancillary organs such as pancreas, liver and gall bladder.

The pharmaceutical composition used in this invention comprises a P2Y purinergic receptor agonist. P2Y agonists increase secretion of water, bicarbonate and mucin in the mucosal epithelia of the gastrointestinal tract. P2Y agonists include uridine 5'- di-and triphosphate (UDP, UTP) and their analogs (Formulae Ia and Ib), adenosine 5'-monophosphate (AMP) and its analogs, adenosine 5'- di-and triphosphate (ADP, ATP) and their analogs (Formulae IIa and IIb), cytidine 5'- di-and triphosphate (CDP, CTP) and their analogs. (Formulae IIIa and IIIb), and dinucleoside polyphosphate compounds (general Formula IV).

BRIEF DESCRIPTION OF THE FIGURES

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Figure 1A:
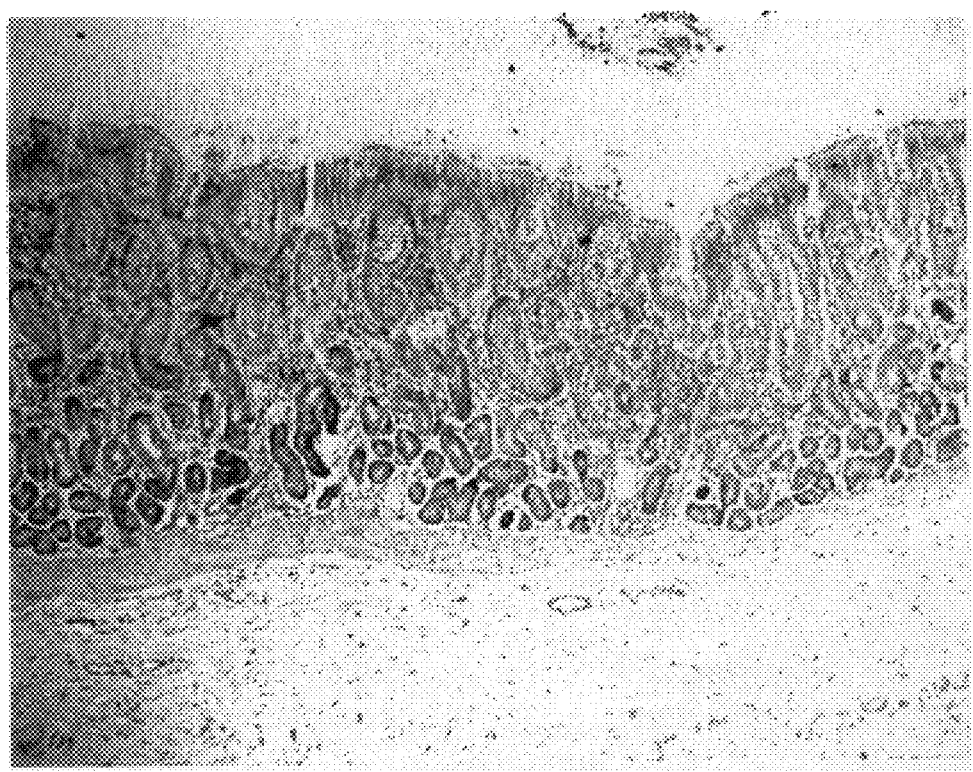
FIG. 1 shows the $P2Y_2$ receptor in situ hybridization results of stomach tissues gastric epithelia) with (a) control sense probe and (b) antisense probe.

The invention provides a method of regulating mucous secretions, bicarbonate secretion, and fluid transport in the gastrointestinal tract. The invention also provides a method of treating gastrointestinal disease in which the mucosal barrier of the organ is impaired, or in which an imbalance of fluid absorption rf secretion occurs in the small and large intestine. The method comprises administering to a mammal a pharmaceutical composition comprising a purinergic P2Y receptor ligand, in an amount effective to regulate mucus or mucin secretions, bicarbonate secretion, or fluid transport in the gastrointestinal tract. The method enhances the mucin release, pH and hydration, or regulates the fluid transport in the gastrointestinal tract.

Gastrointestinal diseases suitable for treatment by this invention include diseases or disorders affecting the buccal cavity (primary salivary), esophagus, stomach, small intestine, large intestine, rectum and ancillary organs such as pancreas, liver and gall bladder. For example, dry mouth, mouth ulcer, gum disease, esophageal reflux disease. peptic ulcer, inflammatory bowel disease (ulcerative colitis and Crohn's disease), mycositis, diarrhea and constipation can be treated by the present method. In addition, gastrointestinal problems associated with cystic fibrosis diseases such as dry mucin and decreased absorption of nutrient by epithelial cells in the gastrointestinal tract can also be treated by the present method. In addition, gastrointestinal problems caused by cancer and chemotherapy can also be treated by this method.

Mucin has been shown to be important in protecting mucosal surfaces from environmental exposure; it acts as an acid barrier and has been found to bind to pathogens. Mucin is thus a part of the natural mucosal defense system in the body, and stimulation of its secretion may lead to protection of the mucosal surface epithelium. The method of the present invention is to increase the mucous secretions in gastrointestinal tracts, such as stomach and esophagus, thus strengthening the natural defense system.

The epithelial lining of the human esophagus consists of squamous epithelium and submucosal glands that serve as a natural barrier between the lumen and blood and act as protective lining against the physical perturbations of the injested food and against the acidic gastric juices from the stomach. The esophageal submucosal glands contain mucous, serous, and myoepithelial cell types. Submucosal glands in the airways and conjunctiva contain $P2Y_2$ receptors in mucosal epithelia of the esophagus. Activation of $P2Y_2$ receptors by natural and synthetic agonists increases mucus secretion into and hydration of the mucosal layer of the esophagus.

A variety of pathophysiological conditions lead to the erosion of the protective mucosal barrier of the esophagus, resulting in gastroesophageal reflux disease (GERD). The symptoms of GERD include mild to severe heartburn, esophageal inflammation (esophagitis), regurgitation, dysfunctional swallowing, and chest pain. GERD is caused by a variety of factors, including abnormal function of the lower esophageal sphincter (which allows reflux of gastric juices into the lower esophagus), delayed stomach emptying, reduced rates of esophageal clearance, and diminished salivation. When the esophagus is exposed to high acid content during gastric reflux, it results in a breakdown of the protective mucus layer. The present invention discloses that in an animal model of esophagitis, $P2Y_2$ receptor agonists can restore the integrity of the disrupted esophageal mucosal layer by naturally stimulating mucin, bicarbonate, and fluid production by squamous epithelia and/or submucosal glands.

Gastric ulcers and gastric reflux are conditions characterized in part by a breakdown in the mucosal defense barrier of the upper gastrointestinal epithelium. Excessive acid secretion in the stomach can lead to a breakdown in the natural mucus layer that protects the epithelial cells from acid damage. Gastric ulcer is associated with, but not limited to stress, diet, *H pylori* infection, chemotherapy or radiotherapy, other autoimmune diseases such as Sjogren's syndrome, etc., surgery, psychosomatic disorders, stress, anxiety, and pharmacological drug-related side effects.

The crypts of Lieberkühn along the small intestine play a principal role in mediating fluid secretion into the lumen of the small intestine. Chloride efflux across apical membrane chloride channels at the apical membrane of epithelial cells along these crypts provide the driving force for osmotically obliged fluid secretion in the small intestine. Constipation and diarrhea result from abnormal fluid transport (absorption verses secretion) across the small and large intestines. The present invention discloses a method to correct for imbalance of fluid transport leading to either constipation or diarrhea by targeting activation of P2Y receptors along the small and large intestines. In pathological conditions, such as exposure to cholera toxin, the apical chloride channels are constitutively active, thus leading to uncontrolled fluid secretion into the small intestine, extreme diarrhea, and mortal bodily dehydration. This observation has provided a scientific rationale for treating constipation and diarrhea.

The activation of chloride and fluid secretion across the small intestines is known to provide additional fluid to chyme before it becomes fecal matter in the large intestine. This addition of fluid to the chyme will thus offset the hyper-absorption of fluid in the large intestine leading to constipation. The present invention discloses that activation of P2Y receptors by agonists provide a mechanism for providing such increase in chloride and fluid secretion into the small intestine and can be used therapeutically to treat constipation.

The colonic epithelia of the large intestine normally absorb fluid and function to remove excessive fluid from the entering chyme from the small intestine and convert it into feces. Diarrhea results from excessive fluid in the entering chyme, or malabsorption of fluid across the colon. Fluid absorption along the colonic epithelia is mediated by sodium absorption via apical membrane sodium channels and basolateral membrane sodium potassium transporters. The fluid absorption properties of this epithelium can be modulated electrogenically by calcium-activated potassium channels at the basolateral membrane. Increase in basolateral membrane potassium conductance hyperpolarizes the apical and basolateral membranes and thus increases the electrogenic driving force for sodium influx across the apical membrane. This results in a concomitant increase in sodium and potassium absorption by the epithelium, and increases ion-coupled fluid absorption. The present invention discloses that activation of P2Y purinoceptors by agonists increases basolateral membrane potassium conductance and facilitates fluid removal from feces. Therefore direct administration of P2Y receptor agonists can be used therapeutically to treat diarrhea.

The present method comprises administering to a patient a pharmaceutical composition that regulates mucus/mucin secretion, hydration and fluid transport in the gastrointestinal tract. The present method has advantages over other commonly used treatments. The method regulates a patient's own production and secretion of mucus as well as the levels of mucosal hydration. Thus the method maintains the natural protective and lubricant characteristics of mucosa of gastrointestinal system and directly addresses the problem resulting from mucus impairment. The present invention is concerned primarily with the treatment of human subjects, but may also be employed for the treatment of other mammalian subjects, such as dogs and cats, for veterinary purposes. Applicants have discovered that (a) many purinergic P2Y receptors ($P2Y_1$, $P2Y_2$, $P2Y_4$, $P2Y_6$, and $P2Y_{11}$,) are present in gastrointestinal tissues such as salivary glands, esophagus, stomach, small intestine, colon, duodenum, and rectum; (b) a potent purinergic receptor agonist increases the secretion of mucin, and regulates fluid transport in the mucosal epithelia of the gastrointestinal tract.

P2Y agonists include nucleoside mono-, di-, and triphosphates and dinucleoside polyphosphates. Nucleoside monophosphates useful in this invention include adenosine 5'-monophosphate (AMP) and its derivatives such as 2-thioether-substituted AMP, e.g., 2-hexylthio AMP (*Br. J Pharmacol.* 118:1959 (1996)). Nucleoside di-and triphosphates useful in this application include uridine 5'-di- and triphosphate (UDP and UTP) and their analogs of general formulae Ia and Ib; adenosine 5'-di- and triphosphate (ADP and ATP) and their analogs of general formulae IIa and IIb; and cytosine 5'-di- and triphosphate (CDP and CTP) and their analogs of general formulae IIa and IIIb.

UDP and its analogs are depicted by general formula Ia:

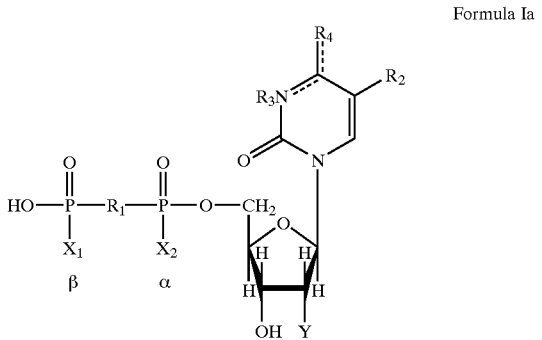

Formula Ia wherein:

$X_1$, and $X_2$ are each independently either $O^-$ or $S^-$;

Y is H or OH;

$R_1$ is selected from the group consisting of O, imido, methylene, and dihalomethylene (e.g., dichloromethylene, difluoromethylene);

$R_2$ is selected from the group consisting of H, halo, alkyl, substituted alkyl, alkoxyl, nitro and azido;

$R_3$ is selected from the group consisting of nothing, H, alkyl, acyl (including arylacyl), and arylalkyl; and $R_4$ is selected from the group consisting of —OR', —SR', NR', and NR'R", wherein R' and R" are independently selected from the group consisting of H, alkyl, substituted alkyl, aryl, substituted aryl, arylalkyl, alkoxyl, and aryloxyl, and with the proviso that R' is absent when $R_4$ is double bonded from an oxygen or sulfur atom to the carbon at the 4-position of the pyrimidine ring.

As used herein, the term "alkyl" refers to $C_{1-10}$ inclusive, linear, branched, or cyclic, saturated or unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, allenyl and optionally substituted arylalkenyl and arylalkyny groups. As used herein, the term "acyl" refers to an organic acid group wherein the —OH of the carboxyl group has been replaced with another substituent (i.e., as represented by RCO—, wherein R is an alkyl or an aryl group). As such, the term "acyl" specifically includes arylacyl groups. Specific examples of acyl groups include acetyl and benzoyl. As used herein, the term "aryl" refers to 5 and 6-membered hydrocarbon and heterocyclic aromatic rings. Specific examples of aryl groups include but are not limited to cyclopentadienyl, phenyl, furan, thiophene, pyrrole, pyran, pyridine, imidazole, isothiazole, isoxazole, pyrazole, pyrazine, pyrimidine, and the like. The term "alkoxyl" as used herein refers to $C_{1-10}$ inclusive, linear, branched, or cyclic, saturated or unsaturated oxo-hydrocarbon chains, including for example methoxy, ethoxy, propoxy, isopropoxy, butoxy, t-butoxy, and pentoxy. The term "aryloxyl" as used herein refers to aryloxy such as phenyloxyl, and alkyl, halo, or alkoxyl substituted aryloxyl. As used herein, the terms "substituted alkyl" and "substituted aryl" include alkyl and aryl groups, as defined herein, in which one or more atoms or functional groups of the aryl or alkyl group are replaced with another atom or functional group, including for example, halogen, aryl, alkyl, alkoxy, hydroxy, nitro, amino, alkylamino, dialkylamino, sulfate, and mercapto. The terms "halo," "halide," or "halogen" as used herein refer to fluoro, chloro, bromo, and iodo groups.

Compounds illustrative of the compounds of Formula (Ia) include those disclosed in WO 99/09998; the reference is incorporated herein by reference. Formula Ia compounds, for example, include: uridine 5'-diphosphate (UDP); uridine 5'-O-(2-thiodiphosphate)(UDPBS); 5-bromouridine 5'-diphosphate (5-BrUDP); 5-(1-phenylethynyl)-uridine 5'-diphosphate (5-(1-phenylethynyl)UDP); 5-methyluridine 5'-diphosphate (5-methylUDP); 4-hexylthiouridine 5'-diphosphate (4-hexylthioUDP); 4-mercaptouridine 5'-diphosphate (4-mercaptoUDP); 4-methoxyuridine 5'-diphosphate (4-methoxyUDP); 4-(N-morpholino)uridine 5'-diphosphate ( 4-(N-morpholino)UDP; 4-hexyloxyuridine 5'-diphosphate (4-hexyloxyUDP); N,N-dimethylcytidine 5'-diphosphate (N,N-dimethylCDP); N-hexylcytidine 5'-diphosphate (N-hexylCDP); and N-cyclopentylcytidine 5'-diphosphate (N-cyclopentylCDP).

Preferred compounds of Formula Ia include UDP and UDPβS and 4-thio UDP. Certain compounds of Formula Ia (e.g., UDP, dUDP, UDPβS, and 4-mercaptoUDP) are known and may be made in accordance with known procedures or variations thereof, which will be apparent to those skilled in the art. For example, the identification and preparation of certain thiophosphate analogues of nucleoside diphosphates (such as UTP-β-S) are set forth in U.S. Pat. No. 3,846,402 (Eckstein et al.), and in R. S. Goody and F. Eckstein, *J Am. Chem. Soc.* 93: 6252–6257 (1971). Alternatively, UDP, and other analogs thereof are also commercially available from vendors such as Sigma (St. Louis, Mo.) and Pharmacia (Uppsala, Sweden).

UTP and its analogs are depicted by general formula Ib;

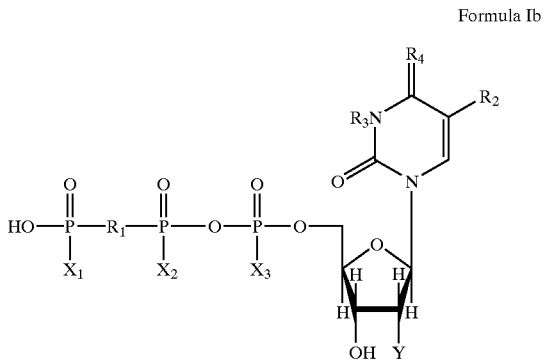

Formula Ib wherein:

$X_1$, $X_2$ and $X_3$ are each independently either $O^-$ or $S^-$,

Y is H or OH;

$R_1$, $R_2$, $R_3$ and $R_4$ are defined as in Formula Ia.

Preferably, $X_2$ and $X_3$ are $O^-$, $R_1$ is oxygen or imido, and $R_2$ is H. Particularly preferred compounds of Formula Ib include uridine 5'-triphosphate (UTP) and uridine 5'-O-(3-thiotriphosphate) (UTPYS).

ADP and its analogs are depicted by general Formula IIa:

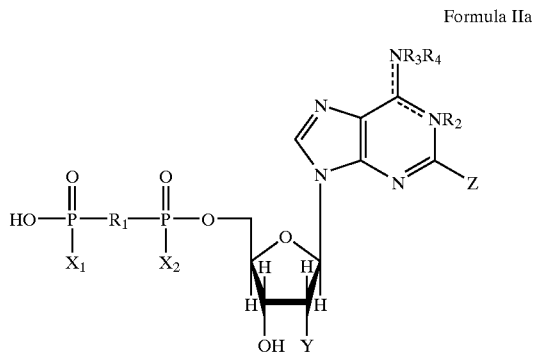

Formula IIa wherein:

R$_1$, X$_1$, X$_2$ and Y are defined as in Formula Ia;

Z is H, Cl, or SR, wherein R is alkyl (C$_1$–C$_{20}$, saturated or unsaturated);

R$_3$ and R$_4$ are H while R$_2$ is nothing and there is a double bond between N-I and C-6 (adenine), or R$_3$ and R$_4$ are H while R$_2$ is nothing and Z is SR, or R$_3$ and R$_4$ are H while R$_2$ is O and there is a double bond between N-1 and C-6(adenine 1-oxide), or R$_3$, R$_4$, and R$_2$ taken together are —CH=CH—, forming a ring from N-6 to N-1 with a double bond between N-6 and C-6 (1,N6-ethenoadenine).

Particularly preferred compounds of Formula IIa include 5'-adenosine diphosphate (ADP) and 2-methyl-SADP.

ATP and its analogs are depicted by general Formula IIb:

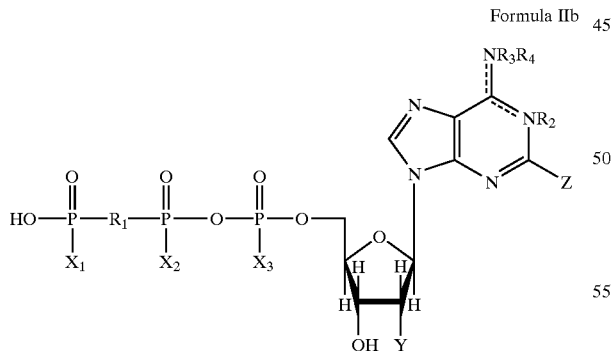

Formula IIb wherein:

R$_1$, X$_1$, X$_2$, X$_3$ and Y are defined as in Formula Ib, and

R$_2$, R$_3$, R$_4$ and Z are defined as in Formula IIa. Preferred compounds of Formula IIb include 5'-adenosine triphosphate (ATP).

CDP and its analogs are depicted by general Formula IIIa:

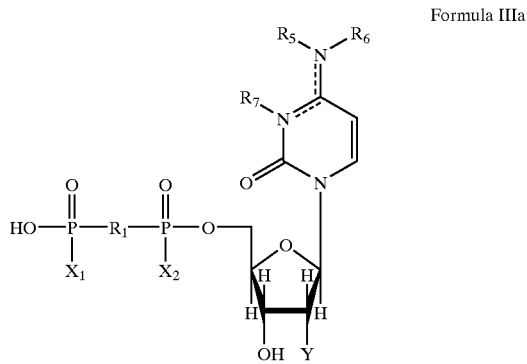

Formula IIIa wherein:

R$_1$, X$_1$, X$_2$ and Y are defined as in Formula Ia;

R$_5$ and R$_6$ are H while R$_7$ is nothing and there is a double bond between N-3 and C-4 (cytosine), or R$_5$, R$_6$ and R$_7$ taken together are —CH=CH—, forming a ring from N-3 to N-4 with a double bond between N-4 and C-4 (3,N$^4$-ethenocytosine), optionally the hydrogen of the 4- or 5-position of the etheno ring is substituted with alkyl, substituted alkyl, aryl, substituted aryl (heteroaryl, etc.), alkoxyl, nitro, halo, or azido.

CTP and its analogs are depicted by general Formula IIIb:

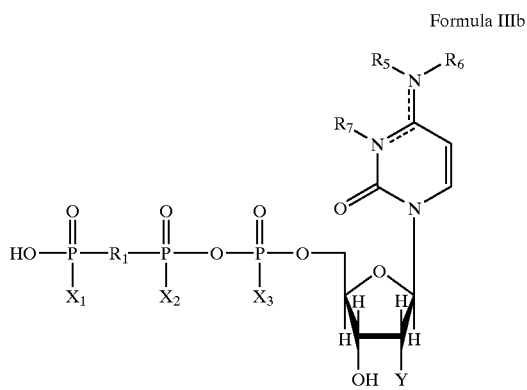

Formula IIIb wherein:

R$_1$, X$_1$, X$_2$, X$_3$ and Y are defined as in Formula Ib, and

R$_5$, R$_6$ and R$_7$ are defined as in Formula IIIa. Preferred compounds of Formula IIIb include cytidine 5'-triphosphate (CTP) and 4-nitrophenyl ethenocytidine 5'-triphosphate.

For simplicity, Formulas I, II, and III, herein illustrate the active compounds in the naturally occurring D-configuration, but the present invention also encompasses compounds in the L-configuration, and mixtures of compounds in the D- and L-configurations, unless otherwise specified. The naturally occurring D-configuration is preferred.

P2Y agonists also include dinucleoside phosphates of general Formula (IV):

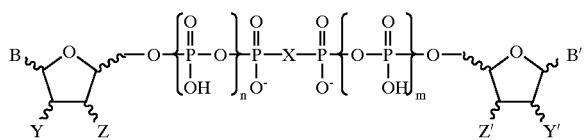

Formula IV wherein:
X is oxygen, methylene, difluoromethylene, or imido;
n=0, 1 or 2;
m=0, 1 or 2;
n+m=0, 1, 2, 3, or 4;
Z=OH or H;
Z'=OH or H;
Y=H or OH;
Y'=H or OH.

The sugar moieties are as depicted in the D-configuration, but may be L-, or D- and L-. The D-configuration is preferred. The nucleoside residue can be in the alpha- or beta- and D- or L-configurations, but most preferably the beta-D-configuration.

B and B' are each independently a purine residue or a pyrimidine residue, as defined in Formula V and VI, respectively, linked through the 9- or I-position, respectively.

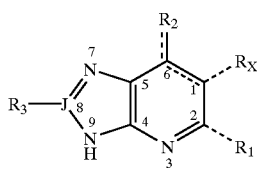

Formula V wherein:
$R_1$ is hydrogen, chlorine, amino, monosubstituted amino, disubstituted amino, alkylthio, arylthio, or aralkylthio, wherein the substituent on sulfur contains up to a maximum of 20 carbon atoms, with or without unsaturation;

$R_2$ is hydroxy, amino, mercapto, alkylthio, arylthio, aralkylthio, acylthio, alkyloxy, aryloxy, aralkyloxy, acyloxy, monosubstituted alkylamino, heterocyclic, monosubstituted cycloalkylamino, monosubstituted aralkylamino, monosubstituted arylamino, diaralkylamino, diarylamino, dialkylamino (wherein alkyl groups are optionally linked to $N_7$ to form a substitute ring), acylamino, diacylamino, or $NHR_y$;

$R_x$ is O (adenine 1-oxide derivatives), or is absent (adenine derivatives);

provided that when $R_2$ is $NHR_y$, $R_y$ and $R_x$ may be taken together form a 5-membered fused imidazole ring (1,$N^6$-ethenoadenine derivatives), optionally substituted on the 4- or 5-positions of the etheno moiety with alkyl, aryl or aralkyl moieties as defined below;

$R_3$ is hydrogen, azido, alkoxy, aryloxy, aralkyloxy, alkylthio, arylthio, or aralkylthio as defined below; or ω-A ($C_{1-6}$-alkyl)OCONH ($C_{1-6}$alkyl)B— wherein A and B are independently amino, mercapto, hydroxy or carboxyl; or pharmaceutically acceptable esters, amides or salts thereof; or absent.

Thus, the substituted derivatives of adenine include adenine 1-oxide; 1,$N^6$-(4- or 5-substituted etheno) adenine; 6-substituted adenine; or 8-substituted aminoadenine, where R' of the 6- or 8-HNR' groups are chosen from among: arylalkyl ($C_{1-6}$) groups with the aryl moiety optionally functionalized as described below; alkyl; and alkyl groups with functional groups therein, such as: ([6-aminohexyl] carbamoylmethyl)-, and ω-acylated- amino(hydroxy, thiol and carboxy)alkyl($C_{2-10}$)—and their ω-acylated-amino (hydroxy, thiol and carboxy) derivatives where the acyl group is chosen from among, but not limited to, acetyl, trifluoroacetyl, benzoyl, substituted-benzoyl, etc., or the carboxylic moiety is present as its ester or amide derivative, for example, the ethyl or methyl ester or its methyl, ethyl or benzamido derivative. The ω-amino(hydroxy, thiol) moiety may be alkylated with a $C_{1-4}$ alkyl group.

J is carbon or nitrogen, with the provision that when J is nitrogen, $R_3$ is not present;

wherein the alkyls are straight-chain, branched or cyclic;
wherein the aryl groups are optionally substituted with lower alkyl, amino, alkylamino, $NO_2$, $N_3$, carboxylic, amido, sulfonamido, or halo groups; and B and B', can also be a pyrimidine with the general formula of Formula VI, linked through the 1- position to ribosyl residue:

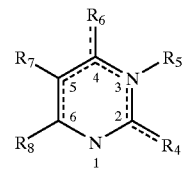

Formula VI wherein:
$R_4$ is hydrogen, hydroxy, oxo, mercapto, amino, cyano, $C_{7-12}$arylalkoxy, $C_{1-6}$, alkylthio, $C_{1-6}$ alkoxy, C, alkylamino, or di$C_{1-4}$alkylamino, wherein the alkyl groups are optionally linked to form a heterocycle;

$R_5$ is hydrogen, oxo, acetyl, benzoyl, $C_{1-6}$ alkyl, $C_{1-5}$ alkanoyl, or aroyl;

$R_6$ is hydroxy, oxo, mercapto, $C_{1-4}$alkoxy, $C_{7-12}$arylalkoxy, $C_{1-6}$alkylthio, amino, S-phenyl, $C_{1-5}$ disubstituted amino, triazolyl, $C_{1-6}$alkylamino, or di-$C_{1-4}$alkylamino, wherein said dialkyl groups are optionally linked to form a heterocycle or linked to $N^3$ to form a substituted ring; or $R_5$ and $R_6$ taken together form a 5-membered fused imidazole ring between positions 3 and 4 of the pyrimidine ring and form a 3,$N^4$-ethenocytosine derivative, wherein said etheno moiety is optionally substituted on the 4- or 5-positions with $C_{1-4}$ alkyl, phenyl or phenyloxy; wherein at least one hydrogen of said $C_{1-4}$ alkyl, phenyl or phenyloxy is optionally substituted with a moiety selected from the group consisting of: halogen, hydroxy, $C_{1-4}$alkoxy, $C_{1-4}$alkyl, $C_{6-10}$aryl, $C_{7-12}$arylalkyl, carboxy, cyano, nitro, sulfonamido, sulfonate, phosphate, sulfonic acid, amino, $C_{1-4}$ alkylamino, and di- $C_{1-4}$ alkylamino, wherein said dialkyl groups are optionally linked to form a heterocycle;

$R_7$ is selected from the group consisting of: hydrogen, hydroxy, cyano, nitro, and $C_{2-8}$ alkenyl; wherein said alkenyl moiety is optionally linked through an oxygen to form a ring, wherein at least one hydrogen of said alkenyl moiety on the carbon adjacent to said oxygen is optionally substituted with a substituent selected from the group consisting of: $C_{1-6}$ alkyl or phenyl; substituted $C_{2-8}$ alkynyl, halogen, substituted $C_{1-4}$alkyl, $CF_3$, $C_{2-3}$ alkenyl, $C_{2-3}$ alkynyl, allylamino, bromovinyl, ethyl propenoate, or propenoic acid; or $R_6$ and $R_7$ together form a 5 or 6-membered saturated or unsaturated ring bonded through N or O or S at $R_6$, such ring optionally contains substituents that themselves contain functionalities; provided that when $R_8$ is amino or substituted amino, $R_7$ is hydrogen; and $R_8$ is selected from the group consisting of: hydrogen, amino or di-$C_{1-4}$alkylamino, $C_{1-4}$alkoxy, $C_{7-12}$arylalkoxy, $C_{1-4}$alkylthio, $C_{7-12}$arylalkylthio, carboxamidomethyl, carboxymethyl, methoxy, methylthio, phenoxy, and phenylthio.

In the general structure of Formulae I-III above, the dotted lines in the 2- to 6- positions are intended to indicate the presence of single or double bonds in these positions; the relative positions of the double or single bonds being determined by whether the $R_4$, $R_5$ and $R_6$ substituents are capable of keto-enol tautomerism.

In the general structures of Formula I-III above, the acyl groups comprise alkanoyl or aroyl groups. The alkyl groups contain 1 to 8 carbon atoms, particularly 1 to 4 carbon atoms optionally substituted by one or more appropriate substituents, as described below. The aryl groups including the aryl moieties of such groups as aryloxy are preferably phenyl groups optionally substituted by one or more appropriate substituents, as described below. The above-mentioned alkenyl and alkynyl groups contain 2 to 8 carbon atoms, particularly 2 to 6 carbon atoms, e.g., ethenyl or ethynyl, optionally substituted by one or more appropriate substituents as described below.

Appropriate substituents on the above-mentioned alkyl, alkenyl, alkynyl, and aryl groups are selected from halogen, hydroxy, $C_{1-4}$ alkoxy, $C_{1-4}$ alkyl, $C_{6-12}$ aryl, $C_{6-12}$ arylalkoxy, carboxy, cyano, nitro, sulfonamido, sulfonate, phosphate, sulfonic, amino and substituted amino wherein the amino is singly or doubly substituted by a $C_{1-4}$ alkyl, and when doubly substituted, the alkyl groups optionally being linked to form a heterocycle.

The invention further provides novel pharmaceutical compositions comprising compounds of general Formula IV, which newly feature: (1) a novel dinucleotide with a sugar moiety selected from the group consisting of: arabinofuranosyl, 3'-deoxyribofuranosyl, xylofuranosyl, and lyxofuranosyl; (2) a novel dinucleotide with an azapurine base; and (3) a novel dinucleotide with a 6-substituted purine. In the first type of novel composition, when the sugar moiety is 3'-deoxyribofuranosyl, Z and Z' are H. In the second type of novel composition with an azapurine base, J is nitrogen and $R_3$ is absent. In the third type of novel composition with the 6-substituted purine, the 6-monosubstituted amino purine base is excluded.

Preferred dinucleoside polyphosphate compounds useful in this invention are $P^1$, $P^4$-di (urdine-5')-tetraphosphate, $dUP_4U$, $U_2P_3$, $U_2P_5$, $dCP_4U$, $CP_4U$, $IP_5I$, $AP_4A$, $CP_3U$, $UP_3A$ and $A_2P_3$.

Some compounds of Formula I, II and III can be made by methods known those skilled in the art; some compounds are commercially available, for example, from Sigma Chemical Co. (St. Louis, Mo. 63178). Compounds of Formulae Ia (UDP and its analogs) can be prepared according to WO 99/09998. Compounds of Formulae Ib, IIb and IIIb (UTP, ATP, CTP and their analogs) can be prepared according to U.S. Pat. No. 5,763,447. Compounds of Formula IV can be made in accordance with known procedures described by Zamecnik, et al., *Proc. Natl. Acad. Sci. USA* 89, 838–42 (1981); and Ng and Orgel, *Nucleic Acids Res.* 15:3572–80 (1987), Pendergast et al., U.S. Pat. No. 5,837,861, or variations thereof.

The compounds of the present invention also encompass their non-toxic pharmaceutically acceptable salts, such as, but not limited to, an alkali metal salt such as sodium or potassium; an alkaline earth metal salt such as manganese, magnesium or calcium; or an ammonium or tetraalkyl ammonium salt, i.e., $NX_4^+$(wherein X is $C_{1-4}$). Pharmaceutically acceptable salts are salts that retain the desired biological activity of the parent compound and do not impart undesired toxicological effects. The present invention also encompasses the acylated prodrugs of the compounds disclosed herein. Those skilled in the art will recognize various synthetic methodologies which may be employed to prepare non-toxic pharmaceutically acceptable salts and acylated prodrugs of the compounds.

The pharmaceutical utility of P2Y agonist compounds of this invention are indicated by the inositol phosphate assay for P2Y activity. This widely used assay, as described in E. Lazarowski, et al., *Brit. J Pharm.* 116, 1619–27 (1995), relies on the measurement of inositol phosphate formation as a measurement of activity of compounds activating receptors linked via G-proteins to phospholipase C.

In addition, the pharmaceutical utility of P2Y agonist compounds of this invention are indicated by the intracellular calcium mobilization assay for P2Y activity. In this assay, cultured cells are stimulated with the increasing concentrations of P2Y receptor agonists. Intracellular calcium levels are monitored by measuring the changes in fluorescence intensity of a calcium-sensitive dye using the FLIPR (Molecular Devices Corp., Sunnyvale, Calif.) or equivalent instrumentation.

P2Y agonist compounds increase mucus production in in vitro preparations of esophageal, gastric mucosal, jujenum, proximal and distal colon epithelia. Mucus secretion can be assayed by a variety of techniques, including impression cytology, enzyme-linked immunosorbent assay (ELISA), and dot blots using mucin-specific antibodies. (See Danjo et al., *Invest. Ophthalmol. Vis. Sci.*, 39: 2602–2609 (1988); Jumblatt et. al., *Invest. Ophthalmol. Vis. Sci.* 40:43–49 (1999); and Jumblatt et. al., *Invest. Ophthalmol. Vis. Sci.* 39: 5803 (1988)). Our results show robust, prolonged, and significant increases in mucus production when P2Y receptor agonists following administration to the luminal surface of epithelial preparations. Mucin production can be repeatedly increased by repetitive stimulation with agonists.

P2Y agonists significantly alter short circuit currents (Isc) in epithelial preparations from the gastrointestinal system, including esophagous, jujenum and proximal and distal colon. The changes in $I_{sc}$ are consistent with increases in transluminal chloride flux or transerosal potassium flux, and are thus expected to mobilize fluid absorption or secretion across the epithelia accordingly.

The effectiveness of P2Y agonists for amelioration of symptoms associated with gastrointestinal disease can be shown in an animal model. For example, *Helicobacter pylori* infection by acetic acid administration to the antral mucosa of cynomolgus monkeys is a model for chronic gastritis; the model shows histological and clinical phenotype similar to those of human gastric ulcers. Oral administration of P2Y receptor agonists to monkeys with gastritis shows significant recovery of staining of periodic acid-Schiff-positive substances and increases anti-mucin immunoreactivity, both of which reflect an increase in mucin secretion. Reduced histological incidents of gastric ulcerations are also an indication of the effectiveness of the P2Y receptor agonists.

The desired compounds of the present invention may be administered orally, systemtically, intra-operatively, or rectally, in dosage unit formulations containing conventional non-toxic pharmaceutically acceptable carriers, adjuvants and vehicles. The term systemic as used herein includes subcutaneous injections, intravenous, intramuscular, intrasternal injection or infusion techniques.

The pharmaceutical formulation in this invention comprises a ligand compound and a pharmaceutically acceptable carrier. One or more ligand compounds may be present in association with one or more non-toxic pharmaceutically acceptable carriers or diluents or adjuvants and, if desired, other active ingredients. One such carrier would be sugars, where the compounds may be intimately incorporated in the matrix through glassification or simply admixed with the carrier (e.g., lactose, sucrose, trehalose, mannitol) or other acceptable excipients for oral or systemic delivery.

For oral use, the pharmaceutical composition is in a suitable form such as tablets, lozenges, aqueous or oily suspensions, viscous gels, chewable gums, dispersible powders or granules, emulsion, hard or soft capsules, syrups or elixirs. Compositions intended for oral use are prepared according to any method known to the art for the manufacture of pharmaceutical compositions. Such compositions may contain one or more agents selected from the group consisting of sweetening agents, flavoring agents, coloring agents and preserving agents in order to provide pharmaceutically elegant and palatable preparations. Tablets usually contain the active ingredient in admixture with non-toxic pharmaceutically acceptable excipients suitable for the manufacture of tablets. These excipients include, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets may be uncoated or they may be coated by known techniques to provide a sustained action over a longer period. For example, a time delay material such as glyceryl monosterate or glyceryl distearate may be employed.

For oral use, hard gelatin capsules are prepared by mixing the active ingredient with an inert solid diluent, for example, calcium carbonate, calcium phosphate or kaolin. Soft gelatin capsules are prepared by mixing the active ingredient with water or an oil medium, for example, peanut oil, liquid paraffin or olive oil.

For oral use, chewable gums are prepared by embedding the active ingredient in gums; the active ingredient is slowly released upon chewing. This form is suitable for treating mouth ulcers.

For oral use, an aqueous suspension is prepared by addition of water to dispersible powders and granules with a dispersing or wetting agent, suspending agent and one or more preservatives. Suspending agents include, for example, sodium carboxymethylcellulose, methylcellulose and sodium alginate. Dispersing or wetting agents include naturally-occurring phosphatides, condensation products of an allylene oxide with fatty acids, condensation products of ethylene oxide with long chain aliphatic alcohols, condensation products of ethylene oxide with partial esters from fatty acids and a hexitol, and condensation products of ethylene oxide with partial esters derived from fatty acids and hexitol anydrides. Preservatives include, for example, ethyl, and n-propyl p-hydroxybenzoate. An aqueous suspension may also contain one or more coloring agents, one or more flavoring agents, and one or more sweetening agents, such as sucrose or saccharin. Those skilled in the art will recognize the many specific excipients and wetting agents encompassed by the general description above.

For systemic administration, the pharmaceutical formulation is prepared in a sterile medium. The active ingredient, depending on the vehicle and concentration used, can either be suspended or dissolved in the vehicle. Adjuvants such as local anaesthetics, preservatives and buffering agents can also be dissolved in the vehicle. The sterile injectable preparation may be a sterile injectable solution or suspension in a non-toxic acceptable diluent or solvent. Among the acceptable vehicles and solvents that may be employed are sterile water, saline solution, or Ringer's solution.

The pharmaceutical application may also be administered in the form of suppositories for rectal administration. These compositions can be prepared by mixing the active ingredient with a suitable non-irritating excipient which is solid at ordinary temperatures but liquid at the rectal temperature and will therefore melt in the rectum to release the compound. Such excipients include cocoa butter and polyethylene glycols.

Dosage levels of the order of from about 10–2000 mg of active ingredients are useful in the treatment of the above-indicated conditions. Preferred doses are about 50–1000 mg, and more preferred doses are about 75–850 mg of active ingredients. These doses can be given several times a day as needed. The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

The invention is illustrated further by the following examples which are not to be construed as limiting the invention in scope or spirit to the specific procedures described in them.

EXAMPLES

Example 1

Identification of P2Y Receptor in Human Tissues

The presence of $P2Y_1$, $P2Y_2$, $P2Y_4$, $P2Y_6$ and $P2Y_{11}$, purinergic receptors in gastrointestinal tissues was determined in vitro using RT-PCR techniques of human RNA purchased from a commercial sources. Human normal stomach poly $A^+$mRNA was purchased from Clontech (Palo Alto, Calif.). First strand cDNA was synthesized (Advantage RT-for PCR kit; Clontech, Palo Alto, Calif.) from 100 ng of stomach polyA$^+$mRNA using an oligo (dT) 18 primer and MMLV reverse transcriptase (60 min, 42° C.). Control reactions in the absence of reverse transcriptase were also carried out. Human normal esophagus, rectum, duodenum and salivary gland cDNA were purchased from Invitrogen (Carlsbad, Calif.). First strand cDNAs for normal human colon, liver, and small intestine were from Clontech's multiple tissue cDNA panels. RT-PCR was performed with stomach tissues and PCR was performed with other tissues.

Sequence specific primers for $P2Y_1$, $P2Y_2$, $P2Y_4$, $P2Y_6$ and $P2Y_{11}$, genes are listed as follows:

$P2Y_1$ (accession number U42029)

forward 5' CGATCTGTATCAGCGTGCTGGTGTG 3', reverse 5' TCTAGAAGCTTTCCTTGTGGCTCGG 3';

$P2Y_2$ (accession number S74902)

forward 5' AGGAGATGTGTTGGGCAGCAGTGAGGAC 3';

reverse 5' ACCAGGGTTTTCTGGCCAACCTGTGACT 3';

P2Y$_4$ (accession number X91852)
forward 5' ATGCAACGGCCACCTACATGTTCC 3';
reverse 5' GTACTCGGCAGTCAGCTTCCAACA 3';
P2Y$_6$ (accession number U52464)
forward 5' ATGGCATGGCTCTCACTGTCATCG 3';
reverse 5' TTGGTGAGCTTCTGGGTCCTGTGAG 3';
P2Y$_{11}$ (accession number AF030335)
forward 5' ATACTGGTGGTTGAGTTCCTGG 3';
reverse 5' ACCAGGCTATACGCTCTGTAGG 3'.

PCR was performed on 3µl of the cDNA of all tissues listed above using the forward and reverse primer sets (1µl of each primer) designed to amplify each P2Y (P2Y$_1$, P2Y$_2$, P2Y$_4$, P2Y$_6$, P2Y$_{11}$) partial cDNA. The reaction also contained 400 mM of each deoxy nucleotide triphosphate, 3.5 mM MgCl$_2$ and 1 µl of the Advantage cDNA polymerase mix (Clontech, Palo Alto, Calif.). The reaction conditions were: initial 2.5 min at 94° C. and then 30 sec at 94° C., 30 sec at either 60° C. (P2Y$_4$, P2Y$_{11}$) or 65° C. (P2Y$_1$, P2Y$_2$, P2Y$_6$), 1 min at 72° C. for 35 cycles and finally, 10 min at 72° C. Some of the PCR products were cloned into the pCR 2.1 -TOPO vector (TOPO TA Cloning kit; Invitrogen, Carlsbad, Calif.) and sequenced completely using an automated DNA sequencer.

All tissues tested were positive for P2Y receptors. The results are summarized in Table 2.

TABLE 2

Identification of P2Y receptor in human tissues.

|  | Human P2Y$_1$ | Human P2Y$_2$ | Human P2Y$_4$ | Human P2Y$_6$ | Human P2Y$_{11}$ |
|---|---|---|---|---|---|
| Stomach | + | + | + | + | + |
| Salivary Gland | + | + | + | + | + |
| Esophagus | + | + | + | + | + |
| Duodenum | + | + | + | + | + |
| Small Intestine | + | + | + | + | + |
| Colon | + | + | + | + | + |
| Rectum | + | + | + | + | + |
| Liver | + | + | + | + | + |
| Pancreas | + | + | + | + | + |

Example 2
Cellular Localization of P2Y Nucleotide Receptor Gene Expression in Monkey Gastrointestical Epithelial Tissues by Nonisotopic In Situ Hybridization Tissues. Study tissues were obtained from Pathology Associates International, Frederick, Md. Tissues included in this study were stomach, esophagus, small intestine (jejunum), and large intestine (colon). Tissues were removed from a 3.25 year old Indian Rhesus Macaque immediately following euthanasia and snap frozen in O.C.T. embedding medium. Frozen tissues were stored at −80° C. prior to cryosectioning. Tissues were cut in 5 µm sections and mounted on microscope slides for hematoxylin & eosin (H&E) staining, and in situ hybridization (ISH).

Assessment of Tissue Sections. H&E-stained tissue sections were prepared to evaluate the quality and orientation of study tissues. Examination of H&E slides indicated that all tissues were suitable for ISH.

Riboprobe Synthesis. A PCR product containing nucleotides 253–651 from a human P2Y$_2$-R cDNA was obtained from a sponsor. P2Y$_2$-R nucleotides 272–627 were reamplified with P2Y$_2$ primers (forward primer sequence: 5'AGGAGATGTGTTGGGCAGCAGT-GAGGAC3' reverse primer sequence: reverse 5'ACCAGGGTTTTCTGGCCAACCTGTGACT3' designed to incorporate either an upstream T3 promotor or a downstream T7 promotor. The resulting PCR products were used to synthesize digoxigenin-labeled riboprobes by in vitro transcription (IVT). Antisense and sense riboprobes were synthesized using T7 and T3 RNA polymerases, respectively, in the presence of digoxigenin-11-UTP (Roche Molecular) using a MEGAscript IVT kit (Ambion) according to the manufacturer. Following IVT, template DNA was degraded with DNase-1, and unincorporated digoxigenin was removed by ultrafiltration. Riboprobe integrity was assessed by electrophoresis through a denaturing polyacrylamide gel. Apparent molecular size was estimated by comparison with the electrophoretic mobility of a 100–1000 base pair RNA ladder (Ambion). Probe yield and labeling was evaluated by blot immunochemistry. Riboprobes were dispensed in 5 µL aliquots and stored at −80° C. until used for ISH.

In Situ hybridization. Frozen tissues were cut into 5 µm sections, mounted on SuperFrost Plus slides (Fisher Scientific), and post-fixed for 15 minutes in 4% paraformaldehyde in PBS at pH 7.4. Tissue sections were then treated for 30 minutes with 0.1% active diethylpyrocarbonate in PBS at pH 7.4. Sections were prehybridized in the absence of probe, then incubated overnight in hybridization buffer containing 400 ng/mL of either antisense or sense probe. Following hybridization, slides were subjected to a series of post-hybridization stringency washes to reduce non-specific staining. Hybridization was visualized by immunohistochemistry using alkaline phosphatase-conjugated anti-digoxigenin Fab and nitroblue tetrazolium chloride-bromochloroindolyl phosphate (Roche Molecular) according to the manufacturer. Tissue sections were counter stained with nuclear fast red. Negative controls included stomach and esophagus tissues stained with the sense P2Y$_2$-R probe.

Figure 1B:
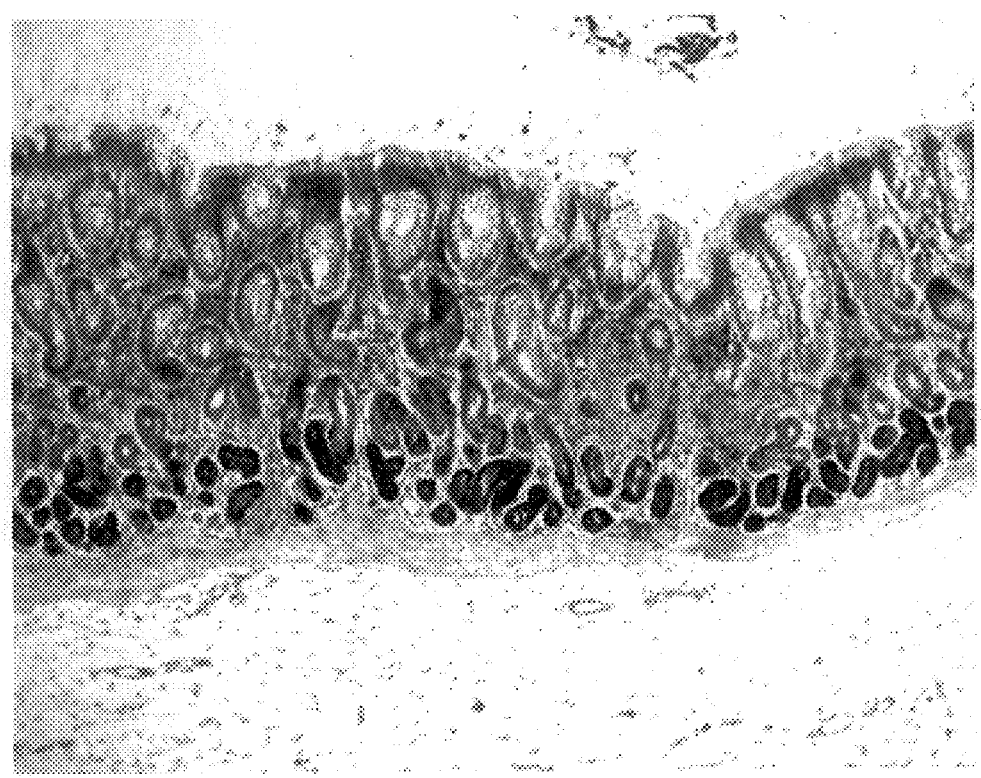
Figure 2A:
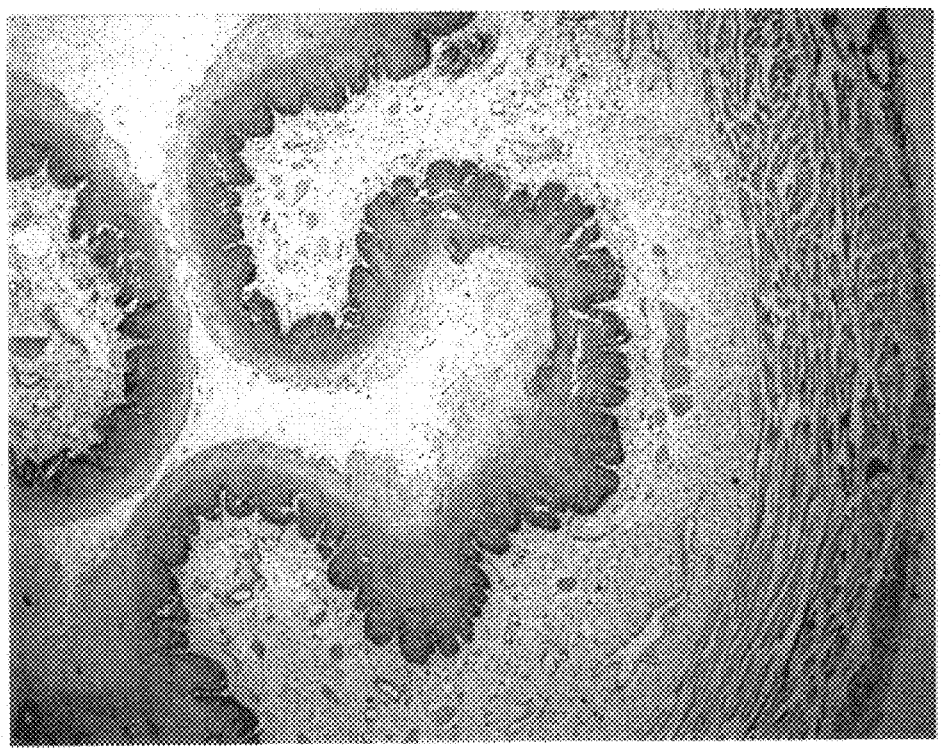
FIG. 2 shows the $P2Y_2$ receptor in situ hybridization results of esophagus pithelia with (a) control sense probe and (b) antisense probe.
Figure 2B:
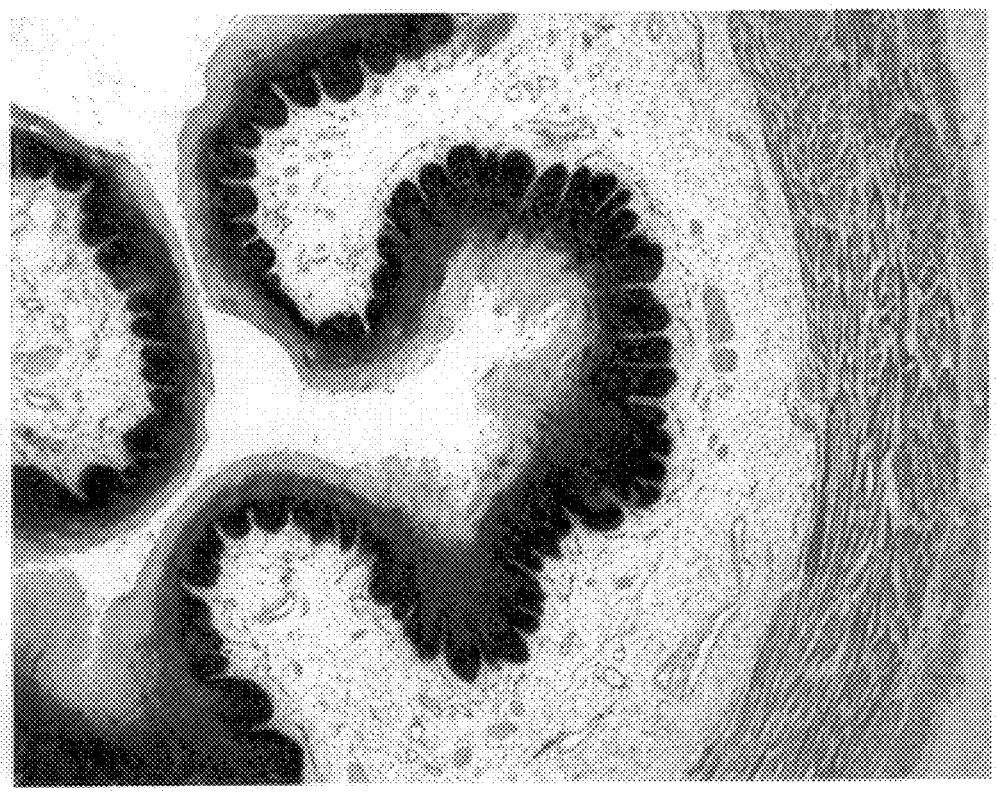
Figure 3A:
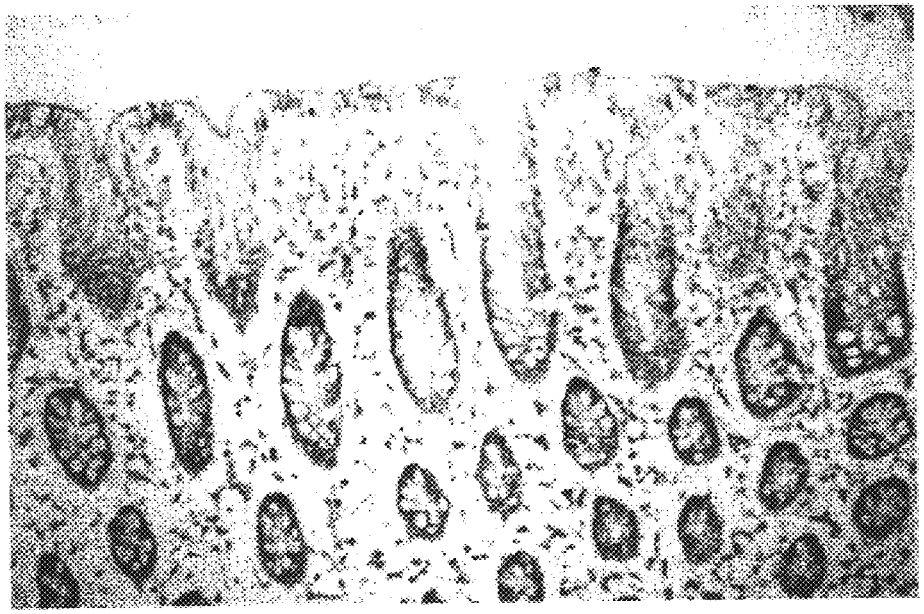
FIG. 3 shows the $P2Y_2$ receptor in situ hybridization results of the large intestine (colon) epithelia with (a) sense probe and (b) antisense probe.
Figure 3B:
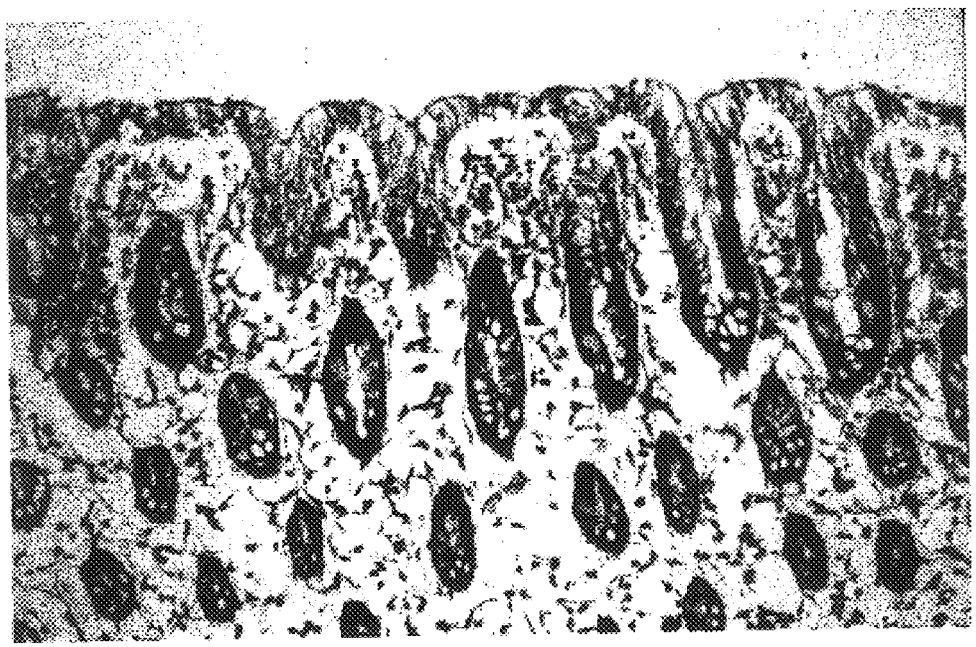
Figure 4A:
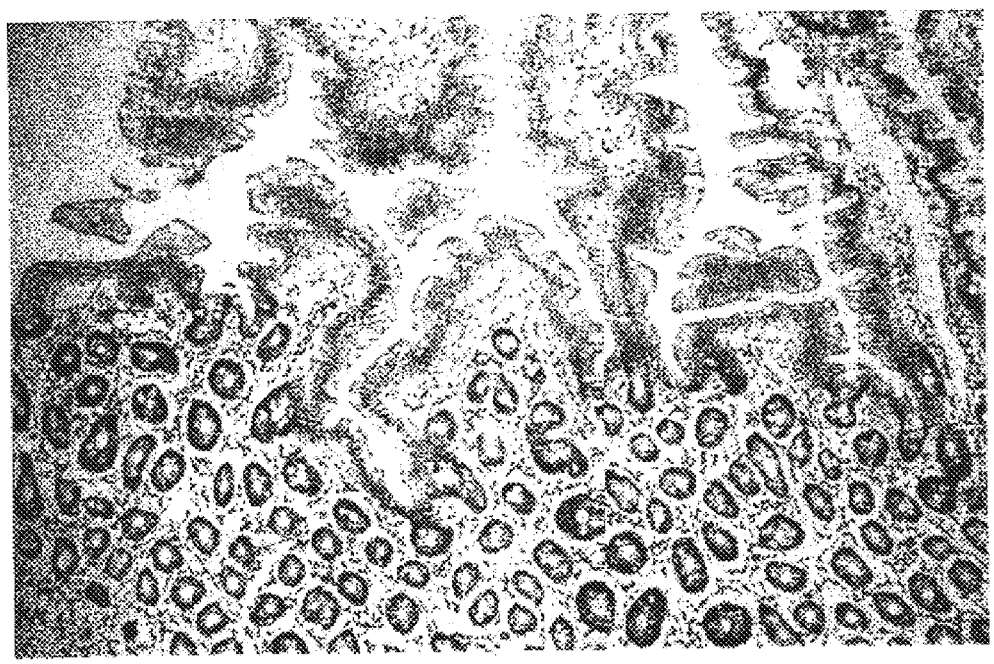
FIG. 4 shows the $P2Y_2$ receptor in situ hybridization results of the small intestine jejunum) epithelia with (a) sense probe and (b) antisense probe.
Figure 4B:
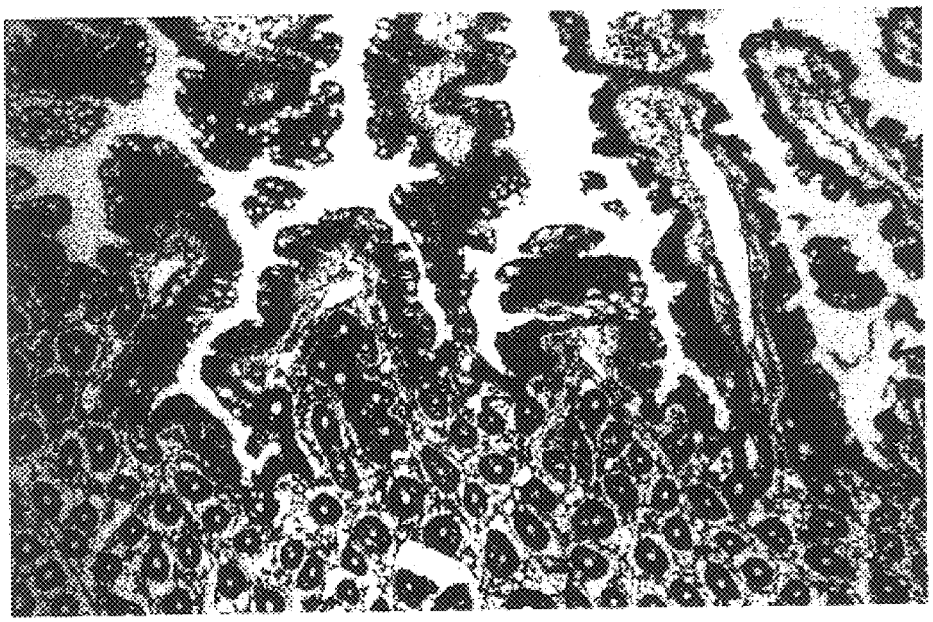

Results. The results from in situ hybridization experiments are shown for the sense probe (negative control) and antisense probe for the stomach (FIG. 1), esophagus (FIG. 2), colon (FIG. 3), and jejunum (FIG. 4). All tissues show positive staining in the mucosal epithelium, indicative of P2Y$_2$ receptor gene expression, with the antisense probe (FIGS. 1b, 2b, 3b, and 4b), whereas no staining was observed with the control sense probe (FIGS. 1a, 2a, 3a, and 4a). More specifically, P2Y$_2$ gene expression was noted in the epithelium of the gastric pit and in the neck and base of the gastric gland in the stomach; in the stratified squamous epithelium of the esophagus; in absorptive enterocytes and mucus-secreting goblet cells of villus epithelium and secretory crypt epithelium of the jejunum; and in columnar absorptive cells, mucus-secreting goblet cells, and secretory enteroendocrine crypt cells of the colon. The demonstration of P2Y$_2$ receptor gene expression in gastrointestinal epithelium, including both secretory and absorptive cell types, supports a role for P2Y$_2$ receptors in gastrointestinal mucosal physiology, and as a target for the treatment of gatrointestinal diseases in which enhanced mucus secretion and/or fluid secretion are therapeutic.

Example 3
Measurement of intracellular calcium mobilization in cultured epithelial cells from the gastrointestinal tract.

A conventional technique is used to detect intracellular calcium mobilization induced by P2Y receptor agonists. The technique is familiar to those well versed in the art. Cells are seeded in 96-well plates and used for calcium mobilization assays. On the day of the assay, the growth medium is aspirated and replaced with a solution of Fluo-3 AM (2.5 μM final concentration) in an assay buffer consisting of (mM): KCl (10.0), NaCl (118), $CaCl_2$(2.5), $MgCl_2$ (1.0), HEPES (20), glucose (10), pH 7.4. Probenecid (Sigma Chemical Co.) is added to the dye load and dye wash medium at a working concentration of 2.5mM to increase dye retention in the cells. After a 60 minute incubation with Fluo-3 AM at 25° C., cells are washed free of dye (Columbus Plate Washer, TECAN U.S., Inc., Research Triangle Park, N.C.) and are stimulated with increasing concentrations of P2Y receptor agonists. Intracellular calcium levels are simultaneously monitored in each well by measuring the changes in fluorescence intensity using the FLIPR (Molecular Devices Corp., Sunnyvale, Calif.).

Figure 5:
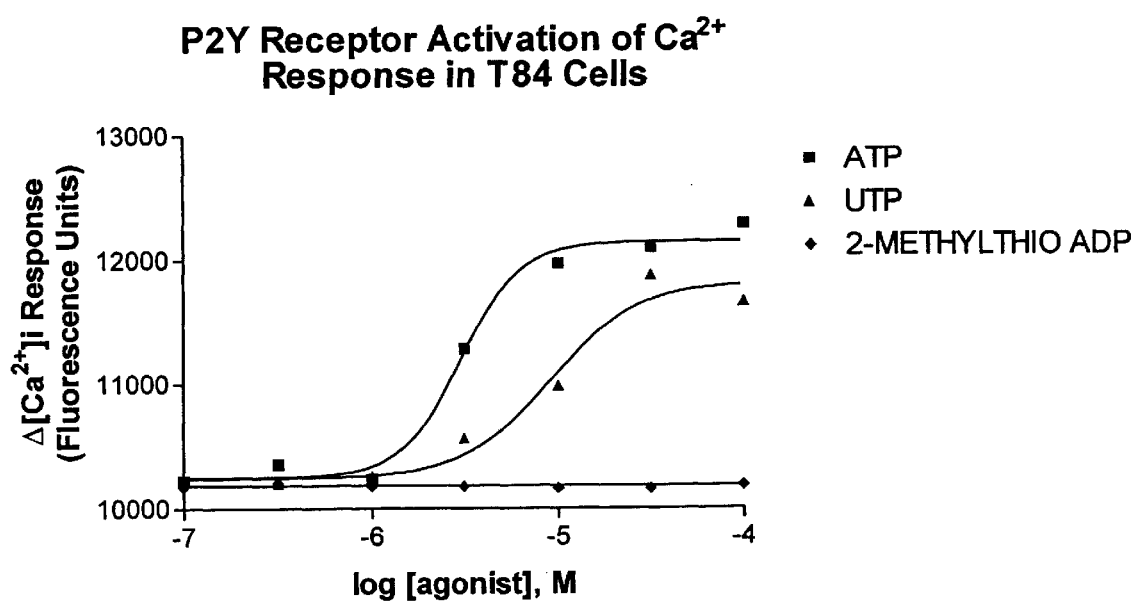
FIG. 5 shows calcium mobilization induced by P2Y receptor agonists in human colonic epithial cells.
Figure 6:
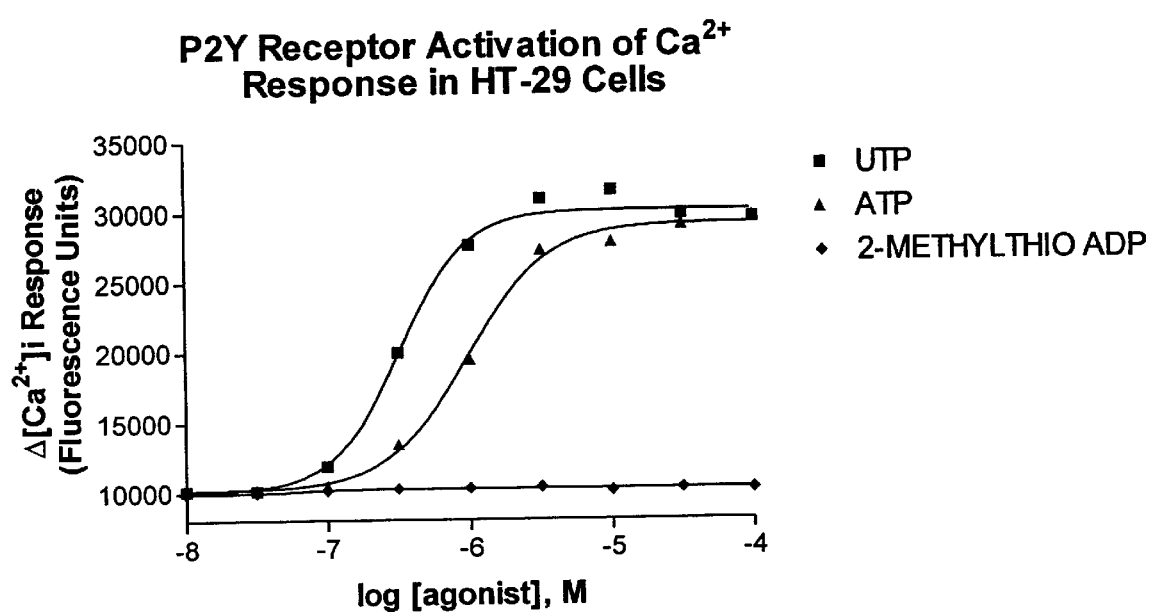
FIG. 6 shows calcium mobilization induced by P2Y receptor agonists in HT-29 human colonic epithelial cells.

T84 cells, a human colonic epithelial cell line, were subjected to the calcium mobilization assay described above. The results show that the P2Y receptor agonists ATP and UTP are stimulate calcium mobilization in these cells, consistent with activation of the $P2Y_2$ receptors (FIG. 5). 2-methylthioADP, a $P2Y_1$ receptor-selective agonist, did not simulate calcium mobilization, indicating the lack of $P2Y_1$ receptors in these cells. Similarly, human colonic HT-29 cells exhibit a robust P2Y response to ATP and UTP, consistent with $P2Y_2$ receptor activation (FIG. 6). The activation of intracellular calcium mobilization by ATP and UTP in T84 and HT-29 cells indicate the pharmaceutical utility of P2Y receptor agonists in the gastrointestinal tract. [UTP-stimulated calcium mobilization has been reported in HT-29 cells: Otero et al. *Mol Cell Biochem* 2000 Feb;205 (1–2):115–23].

Example 4
Measurement of gastrointestinal epithelial mucus production, bicarbonate secretion, and short circuit current in epithelial cultures and explants.

Conventional techniques are used for investigating epithelial electrical responses mediated by agonists of $P2Y_2$ and $P2Y_4$ purinoceptors. The techniques are familiar to those well versed in the art. Native explants and cultured mucosal epithelial cells from the esophagus, stomach, jujenum and colon epithelia are isolated or grown as monolayers, where the integrity of junctional complexes separating apical (mucosal) and basolateral (serosal) membranes remains intact. Epithelial tissues or monolayers are mounted in a modified Ussing chamber that allows for maintenance of epithelial polarity and affords the ability to separately perfuse Ringer's solution to apical and basolateral surfaces. Short-circuit currents and total transepithelial resistances are continuously measured using conventional electrophysiological techniques. Bicarbonate secretion is measured by monitoring pH using a pH-stat system. Changes in these parameters that are consistent with chloride ion secretion, bicarbonate secretion, or alteration of the transmembrane flux of other ions indicate that P2Y receptor agonists modify secretion, absorption, and/or mucosal hydration in the gastrointestinal tract.

Mucus production by goblet cells residing in epithelial glands is assayed by a variety of techniques familiar to those well versed in the art. Native explant and cultured monolayers of esophageal and gastric mucosal epithelia are assayed for mucin production by impression cytology, which consists of exposing fixed surface area of epithelium with polyvinylidene difluoreide (PVDF) membrane and staining PVDF membrane with periodic-acid and Schiff's (PAS) reagent. The amount of PAS-positive staining is inversely proportional to mucin secretion. In esophageal and gastric mucosal epithelia, agonists of $P2Y_2$ and $P2Y_4$ perinoceptors are shown to decrease PAS staining, which is consistent with an increase mucus secretion. P2Y purinoceptor-induced increases in mucus secretion are verified by enzyme-linked immunosorbent assay (ELISA), and immunoblots using mucin-specific antibodies. Positive results indicate robust, prolonged, and significant increases in mucus production when purinoceptor agonists following administered to luminal surface of epithelial preparation. Mucin production can be repeatedly increased by repetitive stimulation with purinoceptor agonists.

Example 5
Purinoceptor agonists for amelioration of symptoms associated with ulcerative colitis.

*Helicobacter pylori* infection by acetic acid administration to the antral mucosa of cynomolgus monkeys is a model for chronic gastritis, and shows histological and clinical phenotype similar to those of human gastric ulcers. Oral administration of P2Y receptor agonists to monkeys with gastritis shows significant recovery of staining of periodic acid-Schiff-positive substances and increases in anti-mucin immunoreactivity, both of which reflect an increase in mucin secretion. Reduced histological incidents of gastric ulcerations are also an indication of the effectiveness of the P2Y receptor agonists.

A human subject, suffering from ulcerative colitis or chronic gastritis, is treated by a method in the present invention. The patient is given an endoscopy, followed with a biopsy of the gastric mucosa. Ulcerative colitis is diagnosed following confirmation of mucosal inflammation and erosion of the gastric mucosal layer. The present invention treats the patient by an oral administration of a suitable formulation of the P2Y-receptor agonist, which coats the esophageal and gastric mucosal layer and stimulates mucous production under the gastric mucosa. The composition is administered as a slow-release oral form, preferable in the form of chewing gum or lozenges, and is administered multiple times during the day as needed. Disease activity is monitored on the basis of the Clinical Activity Index, Endoscopic Index, Histological Index, and Global Efficacy Assessments by the clinical investigator. Improvements in one or more of these parameters indicate that P2Y agonists ameliorate the symptoms of ulcerative colitis.

Example 6
Purinoceptor agonists for altering fluid-absorption by the small intestine and distal colon and for amelioration of symptoms associated with diarrhea or constipation.

A human subject, suffering from either constipation of diarrhea, is treated by methods in the present invention as follows. The patient presenting either diarrhea or constipatory symptoms is given an oral formulation of compound, said compound formulated as tablet that can discharge the active compound in an amount therapeutically and specifically into the small intestine (for constipation) or large intestine (for diarrhea). The activate compound specifically agonizes P2Y receptors in respective tissue and promotes fluid secretion in small intestine and fluid absorption in large intestine. 48 hour stool output, measured in grams, and the duration of diarrhea or constipation, as assessed by patient questionnaire and/or clinical observation, are determined following treatment. Positive results indicate that P2Y agonists are effective in the treatment of diarrhea and/or constipation.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A method of regulating mucus or mucin secretions, bicarbonate secretion or fluid transport in the gastrointestinal tract of a mammal, said method comprising:

administering to said mammal a pharmaceutical composition comprising a purinergic P2Y receptor ligand, in an amount effective to regulate mucus or mucin secretions, bicarbonate secretion or fluid transport in the gastrointestinal tract, wherein said purinergic P2Y receptor agonist is a nucleoside diphosphate selected from the group consisting of compounds of Formula Ia, IIa and IIIa:

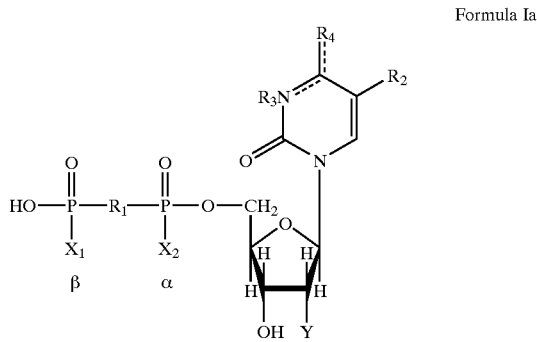

Formula Ia wherein:

$X_1$ and $X_2$ are each independently either $O^-$ or $S^-$;

Y is H or OH;

$R_1$ is selected from the group consisting of O, imido, methylene, and dihalomethylene;

$R_2$ is selected from the group consisting of H, halo, alkyl, substituted alkyl, alkoxyl, nitro and azido;

$R_3$ is selected from the group consisting of H, alkyl, acyl; and

R4 is selected from the group consisting of —OR', —SR', NR', and NR'R", wherein R' and R" are independently selected from the group consisting of H, alkyl, substituted alkyl, aryl, substituted aryl, arylalkyl, alkoxyl, and aryloxyl, and with the proviso that R' is absent when $R_4$ is double bonded from an oxygen or sulfur atom to the carbon at the 4-position of the pyrimidine ring;

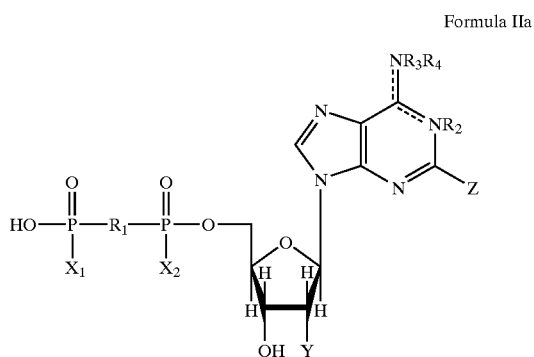

Formula IIa wherein:

$R_1$, $X_1$, $X_2$, and Y are defined as in Formula Ia;

Z is H, Cl, or SR, wherein R is $C_1$–$C_{20}$ saturated or unsaturated alkyl;

$R_3$ and R4 are H while $R_2$ is nothing and there is a double bond between N-1 and C-6, or $R_3$ and R4 are H while $R_2$ is O and there is a double bond between N-1 and C-6, or $R_3$, $R_4$, and $R_2$ taken together are —CH=CH—, forming a ring from N-6 to N-1 with a double bond between N-6 and C-6;

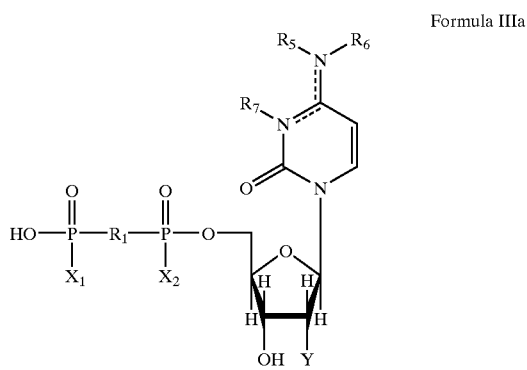

Formula IIIa

Wherein:

$R_1$, $X_1$, $X_2$, and Y are defined as in Formula Ia;

$R_5$ and $R_6$ are H while $R_7$ is nothing and there is a double bond between N-3 and C-4, or $R_5$, $R_6$ and $R_7$ taken together are —CH=CH—, forming a ring from N-3 to N-4 with a double bond between N-4 and C-4, optionally the hydrogen of the 4- or 5-position of the etheno ring is substituted with alkyl, substituted alkyl, alkoxyl, nitro, halo and azido.

2. The method according to claim 1, wherein said nucleotide diphosphate is selected from the group consisting of: 5'-uridine diphosphate, 5'-adenoside diphosphate and 5'-cytidine diphosphate.

3. A method of treating gastrointestinal diseases or disorders in which the mucosal barrier or bicarbonate secretion of the gastrointestinal system is abnormal, or in which the fluid transport across the lumenal tract is abnormal, said method comprising:

administering to a patient a pharmaceutical composition comprising a purinergic P2Y receptor agonist compound, in an amount effective to regulate mucus or mucin secretions or correct abnormal fluid transport in the gastrointestinal system, wherein said purinergic P2Y receptor agonist is a dinucleoside polyphosphate selected from the group consisting of: compounds of Formula IV:

Formula IV

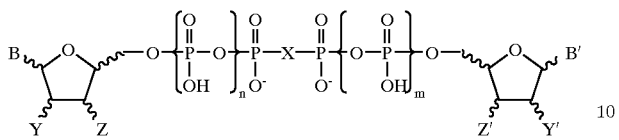

wherein:
X is oxygen, methylene, difluoromethylene, or imido;
n=0, 1 or 2;
m=0, 1 or 2;
n+m=0, 1, 2, 3, or 4;
Z=OH or H;
Z'=OH or H;
Y=H or OH;
Y'=H or OH;
the sugar moieties are D- or L-configuration;
the nucleoside residue is in either the alpha- or beta- and D- or L-configurations;
B and B' are each independently a purine residue or a pyrimidine residue, as defined in Formula V and VI, respectively, linked through the 9- or 1-position, respectively:

Formula V

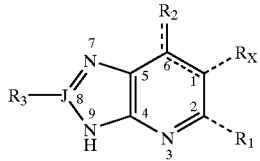

wherein:
$R_1$ is hydrogen, chlorine, amino, monosubstituted amino, disubstituted amino, alkylthio, arylthio, or aralkylthio, wherein the substituent on sulfur contains up to a maximum of 20 carbon atoms, with or without unsaturation;
$R_2$ is hydroxy, amino, mercapto, alkylthio, arylthio, aralkylthio, acylthio, alkyloxy, aryloxy, aralkyloxy, acyloxy, monosubstituted alkylamino, heterocyclic, monosubstituted cycloalkylamino, monosubstituted aralkylamino, monosubstituted arylamino, diaralkylamino, diarylamino, dialkylamino, wherein alkyl groups are optionally linked to $N_7$ to form a substitute ring, acylamino, diacylamino, or $NHR_y$;
$R_x$ is O as in adenine 1-oxide derivatives, or is absent as in adenine derivatives;
provided that when $R_2$ is $NHR_y$, $R_y$ and $R_x$ optionally taken together form a 5-membered fused imidazole ring as in 1, $N^6$-ethenoadenine derivatives, optionally substituted on the 4- or 5-positions of the etheno moiety with alkyl, aryl or aralkyl moieties as defined below;
$R_3$ is hydrogen, azido, alkoxy, aryloxy, aralkyloxy, alkylthio, arylthio, or aralkylthio as defined below; or ω-A($C_{1-6}$alkyl)OCONH ($C_{1-6}$alkyl)B— wherein A and B are independently amino, mercapto, hydroxy or carboxyl; or pharmaceutically acceptable esters, amides or salts thereof; or absent;

wherein the substituted derivative of adenine is adenine 1-oxide; 1,$N^6$-(4- or 5-substituted etheno) adenine; 6-substituted adenine; or 8-substituted aminoadenine, where R' of the 6- or 8-HNR' groups are selected from the group consisting of: arylalkyl ($C_{1-6}$) groups with the aryl moiety optionally functionalized as described below; alkyl; and alkyl groups with functional groups therein, as in: (carbamoylmethyl)—, and ω-acylated-amino(hydroxy, thiol or carboxy)alkyl($C_{2-10}$)— and their ω-acylated-amino (hydroxy, thiol or carboxy) derivatives where the acyl group is selected from the group consisting of acetyl, trifluoroacetyl, benzoyl, substituted-benzoyl, or the carboxylic moiety is present as its ester or amide derivative, such as the ethyl or methyl ester or its methyl, ethyl or benzamido derivative, and the ω-amino(hydroxy, or thiol) moiety is optionally alkylated with a $C_{1-4}$ alkyl group;
J is carbon or nitrogen, with the provision that when J is nitrogen, $R_3$ is not present;
wherein the alkyls are straight-chain, branched or cyclic;
wherein the aryl groups are optionally substituted with lower alkyl, amino, alkylamino, $NO_2$, $N_3$, carboxylic, amido, sulfonamido, or halo groups;

Formula VI

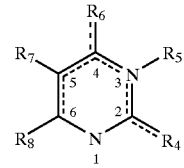

wherein:
$R_4$ is hydrogen, hydroxy, oxo, mercapto, amino, cyano, $C_{7-12}$arylalkoxy, $C_{1-6}$ alkylthio, $C_{1-6}$ alkoxy, $C_{1-6}$ alkylamino, or di$C_{1-4}$alkylamino, wherein the alkyl groups are optionally linked to form a heterocycle;
$R_5$ is hydrogen, oxo, acetyl, benzoyl, $C_{1-6}$ alkyl, $C_{1-5}$ alkanoyl, or aroyl;
$R_6$ is hydroxy, oxo, mercapto, $C_{1-4}$alkoxy, $C_{7-12}$arylalkoxy, $C_{1-6}$alkylthio, amino, S-phenyl, $C_{1-5}$ disubstituted amino, triazolyl, $C_{1-6}$alkylamino, or di-$C_{1-4}$alkylamino, wherein said dialkyl groups are optionally linked to form a heterocycle or linked to $N^3$ to form a substituted ring; or
$R_5$ and $R_6$ taken together form a 5-membered fused imidazole ring between positions 3 and 4 of the pyrimidine ring and form a 3,$N^4$-ethenocytosine derivative, wherein said etheno moiety is optionally substituted on the 4- or 5-positions with $C_{1-4}$ alkyl, phenyl or phenyloxy; wherein at least one hydrogen of said $C_{1-4}$ alkyl, phenyl or phenyloxy is optionally substituted with a moiety selected from the group consisting of: halogen, hydroxy, $C_{1-4}$ alkoxy, $C_{1-4}$ alkyl, $C_{6-10}$ aryl, $C_{7-12}$ arylalkyl, carboxy, cyano, nitro, sulfonamido, sulfonate, phosphate, sulfonic acid, amino, $C_{1-4}$ alkylamino, and di- $C_{1-4}$ alkylamino, wherein said dialkyl groups are optionally linked to form a heterocycle;
$R_7$ is selected from the group consisting of: hydrogen, hydroxy, cyano, nitro, and $C_{2-8}$ alkenyl; wherein said alkenyl moiety is optionally linked through an oxygen to form a ring, wherein at least one hydrogen of said alkenyl moiety on the carbon adjacent to said oxygen is optionally substituted with a substituent selected from the group consisting of: $C_{1-6}$ alkyl or phenyl; substituted $C_{2-8}$ alkynyl, halogen, substituted $C_{1-4}$ alkyl, $CF_3$, $C_{2-3}$ alkenyl, $C_{2-3}$ alkynyl, allylamino, bromovinyl, ethyl propenoate, or propenoic acid; or $R_6$ and $R_7$ together form a 5 or 6-membered saturated or unsaturated ring bonded through N or O or S at $R_6$, such ring optionally contains substituents that themselves contain functionalities; provided that when $R_8$ is amino or substituted amino, $R_7$ is hydrogen; and $R_8$ is selected from the group consisting of: hydrogen, amino or di-$C_{1-4}$alkylamino, $C_{1-4}$alkoxy, $C_{7-12}$arylalkoxy, $C_{1-4}$alkylthio, $C_{7-12}$arylalkylthio, carboxamidomethyl, carboxymethyl, methoxy, methylthio, phenoxy, and phenylthio.

4. The method according to claim 3, wherein said dinucleoside polyphosphate is selected from the group consisting of: $U_2P_4$, $dUP_4U$, $U_2P_3$, $U_2P_5$, $dCP_4U$, $CP_4U$, IP51, $AP_4A$, $CP_3U$, $UP_3A$ and $A_2P_3$.

5. A method of treating gastrointestinal diseases or disorders in which the mucosal barrier or bicarbonate secretion of the gastrointestinal system is abnormal, or in which the fluid transport across the lumenal tract is abnormal, said method comprising:

administering to a patient a pharmaceutical composition comprising a purinergic P2Y receptor agonist compound, in an amount effective to regulate mucus or mucin secretions or correct abnormal fluid transport in the gastrointestinal system, wherein said purinergic P2Y receptor agonist is a nucleoside diphosphate selected from the group consisting of compounds of Formula Ia, IIa and IIIa:

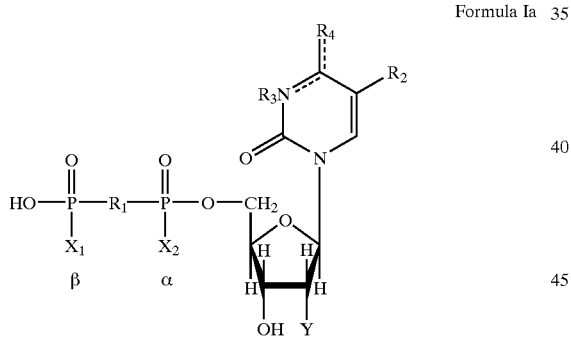

Formula Ia wherein:

$X_1$ and $X_2$ are each independently either $O^-$ or $S^-$;

Y is H or OH;

$R_1$ is selected from the group consisting of O, imido, methylene, and dihalomethylene;

$R_2$ is selected from the group consisting of H, halo, alkyl, substituted alkyl, alkoxyl, nitro and azido;

$R_3$ is selected from the group consisting of H, alkyl, acyl, and arylalkyl; and $R_4$ is selected from the group consisting of —OR', —SR', NR', and NR'R", wherein R' and R" are independently selected from the group consisting of H, alkyl, substituted alkyl, aryl, substituted aryl, arylalkyl, alkoxyl, and aryloxyl, and with the proviso that R' is absent when $R_4$ is double bonded from an oxygen or sulfur atom to the carbon at the 4-position of the pyrimidine ring;

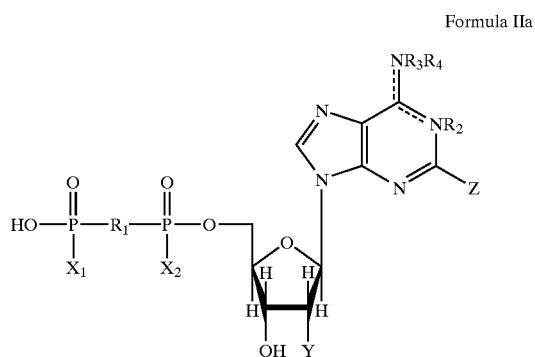

Formula IIa wherein:

$R_1$, $X_1$, $X_2$, and Y are defined as in Formula Ia;

Z is H, Cl, or SR, wherein R is $C_1$–$C_{20}$ saturated or unsaturated alkyl;

$R_3$ and $R_4$ are H while $R_2$ is nothing and there is a double bond between N-1 and C-6, or $R_3$ and $R_4$ are H while $R_2$ is O and there is a double bond between N-1 and C-6, or $R_3$, $R_4$, and $R_2$ taken together are —CH=CH—, forming a ring from N-6 to N-1 with a double bond between N-6 and C-6;

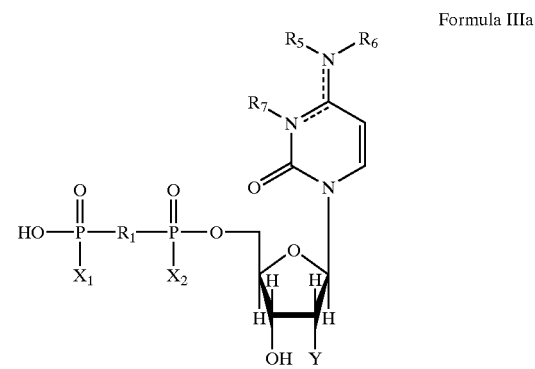

Formula IIIa wherein:

$R_1$, $X_1$, $X_2$, and Y are defined as in Formula Ia;

$R_5$ and $R_6$ are H while $R_7$ is nothing and there is a double bond between N-3 and C-4, or $R_5$, R6 and $R_7$ taken together are —CH=CH—, forming a ring from N-3 to N-4 with a double bond between N-4 and C-4, optionally the hydrogen of the 4- or 5-position of the etheno ring is substituted with alkyl, substituted alkyl, alkoxyl, nitro, halo and azido.

6. A method of treating gastrointestinal diseases or disorders in which the mucosal barrier or bicarbonate secretion of the gastrointestinal system is abnormal, or in which the fluid transport across the lumenal tract is abnormal, said method comprising:

administering to a patient a pharmaceutical composition comprising a purinergic P2Y receptor agonist compound, in an amount effective to regulate mucus or mucin secretions or correct abnormal fluid transport in the gastrointestinal system, wherein said purinergic P2Y receptor agonist is a nucleotide triphosphate selected from the group consistingof: compounds of Formula Ib, IIb and IIIb:

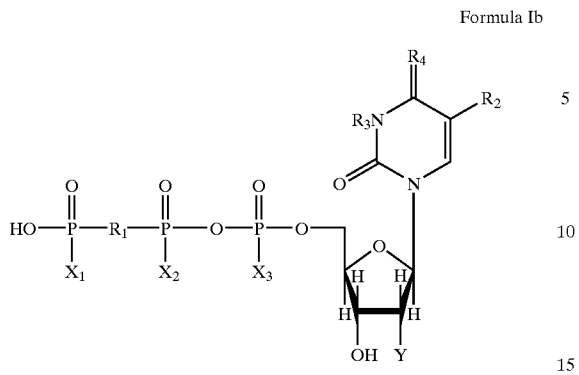

Formula Ib

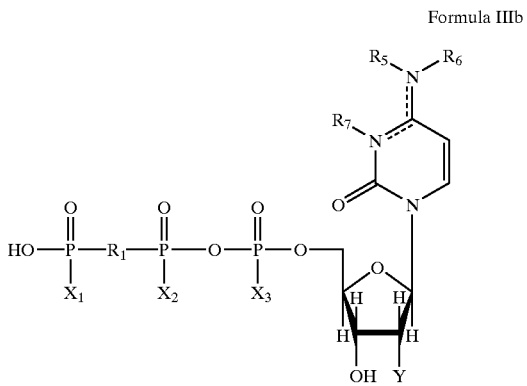

Formula IIIb wherein:

$X_1$, $X_2$ and $X_3$ are each independently either $O^-$ or $S^-$,

Y is H or OH;

$R_1$ is O, imido, methylene or dihalomethylene;

$R_2$ is H or Br;

$R_3$ is selected from the group consisting of nothing, H, alkyl, acyl and arylalkyl; and $R_4$ is selected from the group consisting of —OR', —SR', NR', and NR'R'', wherein R' and R'' are independently selected from the group consisting of H, alkyl, substituted alkyl, aryl, substituted aryl, arylalkyl, alkoxyl, and aryloxyl, and with the proviso that R' is absent when $R_4$ is double bonded from an oxygen or sulfur atom to the carbon at the 4-position of the pyrimidine ring;

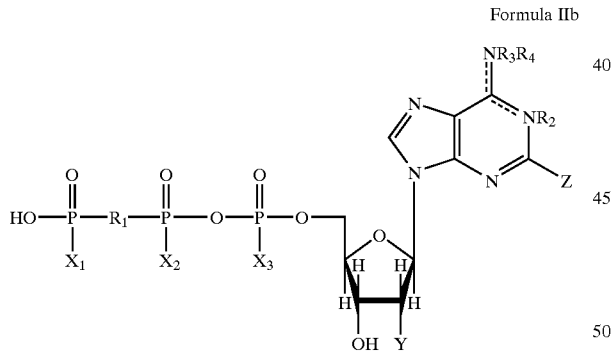

Formula IIb wherein:

$R_1$, $X_1$, $X_2$, $X_3$ and Y are defined as in Formula lb,

Z is H, Cl, or SR, wherein R is $C_1$–$C_{20}$ saturated or unsaturated alkyl;

$R_3$ and R4 are H while $R_2$ is nothing and there is a double bond between N-1 and C-6, or $R_3$ and $R_4$ are H while $R_2$ is O and there is a double bond between N-1 and C-6, or $R_3$, $R_4$ and $R_2$ taken together are —CH=CH—, forming a ring from N-6 to N-1 with a double bond between N-6 and C-6;

wherein:

$R_1$, $X_1$, $X_2$, $X_3$, and Y are defined as in Formula Ib, and $R_5$ and $R_6$ are H while $R_7$ is nothing and there is a double bond between N-3 and C-4, or $R_5$, R6 and $R_7$ taken together are —CH=CH—, forming a ring from N-3 to N-4 with a double bond between N-4 and C-4, optionally the hydrogen of the 4- or 5-position of the etheno ring is substituted with alkyl, substituted alkyl, alkoxyl, nitro, halo and azide.

7. A method of treating dry mouth in a patient in need of such treatment, said method comprising:

administering to the patient a pharmaceutical composition comprising a purinergic P2Y receptor agonist compound, in an amount effective to regulate mucus or mucin secretions or correct abnormal fluid transport in the gastrointestinal system, wherein said purinergic P2Y receptor agonist is a nucleoside triphosphate selected from the group consisting of:

(1) compounds of Formula Ia, IIa and IIIa:

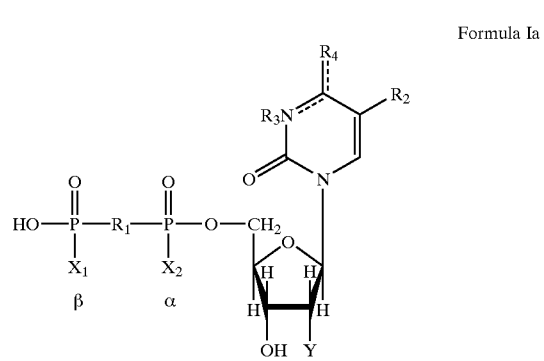

Formula Ia wherein:

$X_1$, and $X_2$ are each independently either $O^-$ or $S^-$;

Y is H or OH;

$R_1$ is selected from the group consisting of O, imido, methylene, and dihalomethylene;

$R_2$ is selected from the group consisting of H, halo, alkyl, substituted alkyl, alkoxyl, nitro and azido;

$R_3$ is selected from the group consisting of H, alkyl, acyl, and arylalkyl; and R4 is selected from the group consisting of —OR', —SR', NR', and NR'R'', wherein R' and R'' are independently selected from the group consisting of H, alkyl, substituted alkyl, aryl, substituted aryl, arylalkyl, alkoxyl, and aryloxyl, and with the proviso that R' is absent when $R_4$ is double bonded from an oxygen or sulfur atom to the carbon at the 4-position of the pyrimidine ring;

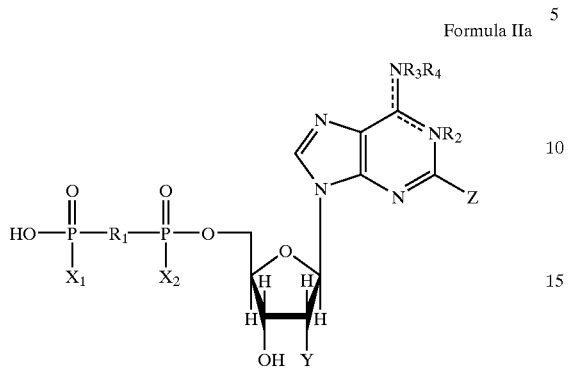

Formula IIa wherein:

$R_1$, $X_1$, $X_2$, and Y are defined as in Formula Ia;

Z is H, Cl, or SR, wherein R is $C_1$–$C_{20}$ saturated or unsaturated alkyl;

$R_3$ and R4 are H while $R_2$ is nothing and there is a double bond between N-1 and C-6, or $R_3$ and $R_4$ are H while $R_2$ is O and there is a double bond between N-1 and C-6, or $R_3$, R4, and $R_2$ taken together are —CH=CH—, forming a ring from N-6 to N-1 with a double bond between N-6 and C-6;

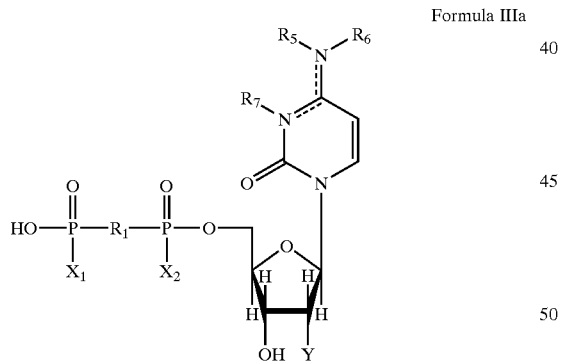

Formula IIIa wherein:

$R_1$, $X_1$, $X_2$, and Y are defined as in Formula Ia;

$R_5$ and $R_6$ are H while $R_7$ is nothing and there is a double bond between N-3 and C-4, or $R_5$, $R_6$ and $R_7$ taken together are —CH=CH—, forming a ring from N-3 to N-4 with a double bond between N-4 and C-4, optionally the hydrogen of the 4- or 5-position of the etheno ring is substituted with alkyl, substituted alkyl, alkoxyl, nitro, halo or azido;

(2) compounds of Formula Ib, IIb and IIIb:

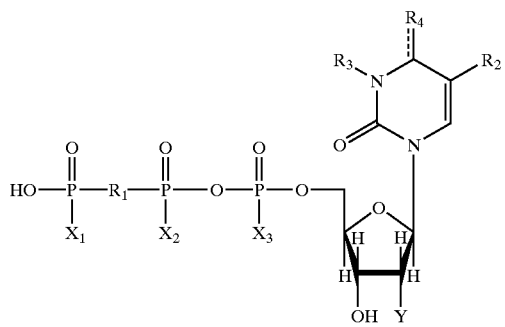

Formula Ib wherein:

$X_1$, $X_2$ and $X_3$ are each independently either $O^-$ or $S^-$,

Y is H or OH;

$R_1$ is O, imido, methylene or dihalomethylene;

$R_2$ is H or Br;

$R_3$ is selected from the group consisting of nothing, H, alkyl, acyl and arylalkyl; and $R_4$ is selected from the group consisting of —OR', —SR', NR', and NR'R", wherein R' and R" are independently selected from the group consisting of H, alkyl, substituted alkyl, aryl, substituted aryl, arylalkyl, alkoxyl, and aryloxyl, and with the proviso that R' is absent when $R_4$ is double bonded from an oxygen or sulfur atom to the carbon at the 4-position of the pyrimidine ring;

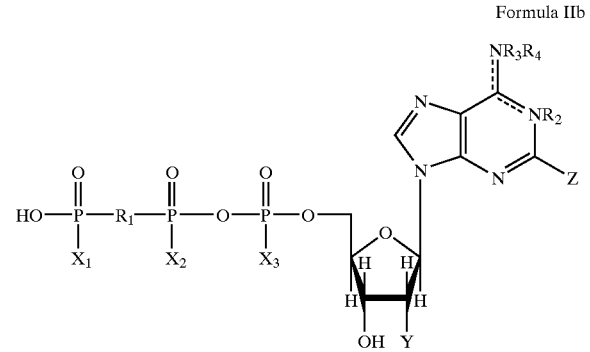

Formula IIb wherein:

$R_1$, $X_1$, $X_2$, $X_3$ and Y are defined as in Formula Ib,

Z is H, Cl, or SR, wherein R is $C_1$–$C_{20}$ saturated or unsaturated alkyl;

$R_3$ and $R_4$ are H while $R_2$ is nothing and there is a double bond between N-1 and C-6, or $R_3$ and $R_4$ are H while $R_2$ is O and there is a double bond between N-1 and C-6, or $R_3$, $R_4$ and $R_2$ taken together are —CH=CH—, forming a ring from N-6 to N-1 with a double bond between N-6 and C-6;

Formula IIIb

[Structure: Cytidine triphosphate analog with R5, R6 on N4; R7 on N3; phosphate chain HO-P(=O)(X1)-R1-P(=O)(X2)-O-P(=O)(X3)-O-sugar with OH and Y positions]

wherein:
$R_1$, $X_1$, $X_2$, $X_3$, and Y are defined as in Formula Ib, and $R_5$ and $R_6$ are H while $R_7$ is nothing and there is a double bond between N-3 and C-4, or $R_5$, $R_6$ and $R_7$ taken together are —CH=CH—, forming a ring from N-3 to N-4 with a double bond between N-4 and C-4, optionally the hydrogen of the 4- or 5-position of the etheno ring is substituted with alkyl, substituted alkyl, alkoxyl, nitro, halo and azide; and (3) compounds of Formula IV:

Formula IV

[Structure: B-sugar(Y,Z)-O-[P(=O)(OH)-O]n-P(=O)(O⁻)-X-P(=O)(O⁻)-[O-P(=O)(OH)]m-O-sugar(Z',Y')-B']

wherein:
X is oxygen, methylene, difluoromethylene, or imido;
n=0, 1 or 2;
m=0, 1 or 2;
n+m=0, 1, 2, 3, or 4;
Z=OH or H;
Z'=OH or H;
Y=H or OH;
Y'=H or OH;
the sugar moieties are D- or L-configuration;
the nucleoside residue is in either the alpha- or beta- and D- or L-configurations;
B and B' are each independently a purine residue or a pyrimidine residue, as defined in Formula V and VI, respectively, linked through the 9- or 1-position, respectively:

Formula V

[Structure: Purine ring with R2 at position 6, Rx at position 5/1, R3-J at position 8, positions numbered 1-9, NH at 7, R1 at position 2]

wherein:
$R_1$ is hydrogen, chlorine, amino, monosubstituted amino, disubstituted amino, alkylthio, arylthio, or aralkylthio, wherein the substituent on sulfur contains up to a maximum of 20 carbon atoms, with or without unsaturation;

$R_2$ is hydroxy, amino, mercapto, alkylthio, arylthio, aralkylthio, acylthio, alkyloxy, aryloxy, aralkyloxy, acyloxy, monosubstituted alkylamino, heterocyclic, monosubstituted cycloalkylamino, monosubstituted aralkylamino, monosubstituted arylamino, diaralkylamino, diarylamino, dialkylamino, wherein alkyl groups are optionally linked to $N_7$ to form a substitute ring, acylamino, diacylamino, or $NHR_y$;

$R_x$ is O as in adenine 1-oxide derivatives, or is absent as in adenine derivatives;

provided that when $R_2$ is $NHR_Y$, $R_y$ and $R_x$ optionally taken together form a 5-membered fused imidazole ring as in 1, $N^6$-ethenoadenine derivatives, optionally substituted on the 4- or 5-positions of the etheno moiety with alkyl, aryl or aralkyl moieties as defined below;

$R_3$ is hydrogen, azido, alkoxy, aryloxy, aralkyloxy, alkylthio, arylthio, or aralkylthio as defined below; or ω-A($C_{1-6}$alkyl)OCONH ($C_{1-6}$alkyl)B— wherein A and B are independently amino, mercapto, hydroxy or carboxyl; or pharmaceutically acceptable esters, amides or salts thereof; or absent;

wherein the substituted derivative of adenine is adenine 1-oxide; 1,$N^6$-(4- or 5-substituted etheno) adenine; 6-substituted adenine; or 8-substituted aminoadenine, where R' of the 6- or 8-HNR' groups are selected from the group consisting of: arylalkyl ($C_{1-6}$) groups with the aryl moiety optionally functionalized as described below; alkyl; and alkyl groups with functional groups therein, as in: (carbamoylmethyl)-, and ω-acylated-amino(hydroxy, thiol or carboxy)alkyl($C_{2-10}$)— and their ω-acylated-amino (hydroxy, thiol or carboxy) derivatives where the acyl group is selected from the group consisting of acetyl, trifluoroacetyl, benzoyl, substituted-benzoyl, or the carboxylic moiety is present as its ester or amide derivative, such as the ethyl or methyl ester or its methyl, ethyl or benzamido derivative, and the e-amino(hydroxy, or thiol) moiety is optionally alkylated with a $C_{1-4}$ alkyl group;

J is carbon or nitrogen, with the provision that when J is nitrogen, $R_3$ is not present;
wherein the alkyls are straight-chain, branched or cyclic;
wherein the aryl groups are optionally substituted with lower alkyl, amino, alkylamino, $NO_2$, $N_3$, carboxylic, amido, sulfonamido, or halo groups Formula VI

[Structure: Pyrimidine ring with R6 at position 4, R7 at position 5, R5 at position 3, R8 at position 6, R4 at position 2, N at positions 1 and 3]

wherein:
$R_4$ is hydrogen, hydroxy, oxo, mercapto, amino, cyano, $C_{7-12}$arylalkoxy, $C_{1-6}$ alkylthio, $C_{1-6}$ alkoxy, $C_{1-6}$ alkylamino, or di$C_{1-4}$alkylamino, wherein the alkyl groups are optionally linked to form a heterocycle;

$R_5$ is hydrogen, oxo, acetyl, benzoyl, $C_{1-6}$ alkyl, $C_{1-5}$ alkanoyl, or aroyl;

$R_6$ is hydroxy, oxo, mercapto, $C_{1-4}$alkoxy, $C_{7-12}$arylalkoxy, $C_{1-6}$alkylthio, amino, S-phenyl, $C_{1-5}$ disubstituted amino, triazolyl, $C_{1-6}$alkylamino, or di-$C_{1-4}$alkylamino, wherein said dialkyl groups are optionally linked to form a heterocycle or linked to $N^3$ to form a substituted ring; or $R_5$ and $R_6$ taken together form a 5-membered fused imidazole ring between positions 3 and 4 of the pyrimidine ring and form a 3,$N^4$-ethenocytosine derivative, wherein said etheno moiety is optionally substituted on the 4- or 5-positions with $C_{1-4}$ alkyl, phenyl or phenyloxy; wherein at least one hydrogen of said $C_{1-4}$ alkyl, phenyl or phenyloxy is optionally substituted with a moiety selected from the group consisting of: halogen, hydroxy, $C_{1-4}$ alkoxy, $C_{1-4}$ alkyl, $C_{6-10}$ aryl, $C_{7-12}$ arylalkyl, carboxy, cyano, nitro, sulfonamido, sulfonate, phosphate, sulfonic acid, amino, $C_{1-4}$ alkylamino, and di- $C_{1-4}$ alkylamino, wherein said dialkyl groups are optionally linked to form a heterocycle;

$R_7$ is selected from the group consisting of: hydrogen, hydroxy, cyano, nitro, and $C_{2-8}$ alkenyl; wherein said alkenyl moiety is optionally linked through an oxygen to form a ring, wherein at least one hydrogen of said alkenyl moiety on the carbon adjacent to said oxygen is optionally substituted with a substituent selected from the group consisting of: $C_{1-6}$ alkyl or phenyl; substituted $C_{2-8}$ alkynyl, halogen, substituted $C_{1-4}$ alkyl, $CF_3$, $C_{2-3}$ alkenyl, $C_{2-3}$ alkynyl, allylamino, bromovinyl, ethyl propenoate, or propenoic acid; or $R_6$ and $R_7$ together form a 5 or 6-membered saturated or unsaturated ring bonded through N or O or S at $R_6$, such ring optionally contains substituents that themselves contain functionalities; provided that when $R_8$ is amino or substituted amino, $R_7$ is hydrogen; and $R_8$ is selected from the group consisting of: hydrogen, amino or di-$C_{1-4}$alkylamino, $C_{1-4}$alkoxy, $C_{7-12}$arylalkoxy, $C_{1-4}$alkylthio, $C_{7-12}$arylalkylthio, carboxamidomethyl, carboxymethyl, methoxy, methylthio, phenoxy, and phenylthio.

8. The method according to claim 1 or 5, wherein said nucleoside diphosphate is selected from the group consisting of: 5'- uridine diphosphate, 5'- adenosine diphosphate and 5'-cytidine diphosphate.

9. The method according to claim 1, 3, or 5, wherein said administering is administering an oral form of said pharmaceutical composition, such that a therapeutically effective amount of said compound contacts the tissues of said gastrointestinal system of said mammal.

10. The method according to claim 1, 3, or 5, wherein said administering is injecting said pharmaceutical composition in an injectable form, such that a therapeutically effective amount of said compound contacts the tissues of said gastrointestinal system via systemic absorption and circulation.

11. The method according to claim 1, 3, or 5, wherein said administering is accomplished by administering a suppository form of said pharmaceutical composition, such that a therapeutically effective amount of said compound contacts the tissues of said gastrointestinal system via systemic absorption and circulation.

12. The method according to claim 3 or 5, wherein said gastrointestinal disorder is gastroesophageal reflux disease.

13. The method according to claim 3, 5 or 6, wherein said gastrointestinal disorder is gastroesophageal reflux disease.

* * * * *

UNITED STATES PATENT AND TRADEMARK OFFICE
CERTIFICATE OF CORRECTION

PATENT NO. : 6,624,150 B2
APPLICATION NO. : 09/747777
DATED : September 23, 2003
INVENTOR(S) : Benjamin R. Yerxa et al.

It is certified that error appears in the above-identified patent and that said Letters Patent is hereby corrected as shown below:

Column 1, line 8, replace "is" with --are--;
Column 1, line 9, replace "its" with --their--.
Column 2, line 17, change "epithelium." to --epithelium,--.
Column 4, line 16, after "to" delete --a--;
Column 4, line 44, change "agonsists" to --agonists--.
Column 8, lines 24-25, "analogs." to --analogs--;
Column 8, line 34, change "gastric epithelia)" to --(gastric epithelia)--;
Column 8, line 37, change "pithelia" to --epithelia--;
Column 8, line 44, change "jejunum)" to --(jejunum)--.
Column 9, line 4, change "disease." to --disease,--;
Column 9, line 27, change "injested" to --ingested--.
Column 10, line 4, change "verses" to --versus--.
Column 12, line 67, change "(UTPYS)." to --UTPγS).--.
Column 15, lines 30-38, change formula from:

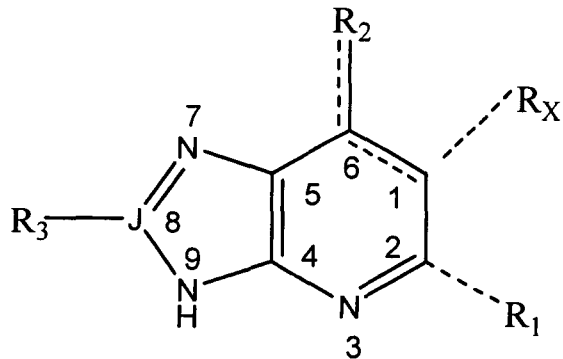

to:

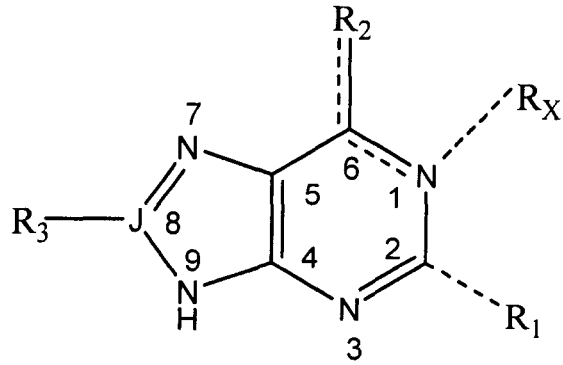

UNITED STATES PATENT AND TRADEMARK OFFICE
CERTIFICATE OF CORRECTION

PATENT NO.        : 6,624,150 B2
APPLICATION NO.   : 09/747777
DATED             : September 23, 2003
INVENTOR(S)       : Benjamin R. Yerxa et al.

It is certified that error appears in the above-identified patent and that said Letters Patent is hereby corrected as shown below:

Column 16, line 33, after "alkoxy," change "C," to --$C_{1-6}$--.
Column 17, line 9, change "structure" to --structures--;
Column 17, line 53, between "known" and "those" add -- to--.
Column 20, line 44, after "from" delete "a".
Column 21, line 46, change "Gastrointestical" to --Gastrointestinal --.
Column 22, line 2, change " 5'ACCAGGGTTTTCTGGCCAACCTGTGACT3' " to
-- 5'ACCAGGGTTTTCTGGCCAACCTGTGACT3')--.
Column 23, line 26, after "UTP" delete "are".
Column 24, line 3, change "difluoreide" to --difluoride--;
Column 24, line 8, change "perinoceptors" to --purinoceptors --;
Column 24, line 9, after "increase" add --in --;
Column 24, line 43, change "preferable" to --preferably--;
Column 24, line 52, change "fluid-" to --fluid--;
Column 24, line 62, change "activate" to --active--.
At Claim 1, Column 26, line 21, change "R4" to --$R_4$--;
At Claim 1, Column 26, line 23, change "R4" to --$R_4$--.

UNITED STATES PATENT AND TRADEMARK OFFICE
CERTIFICATE OF CORRECTION

PATENT NO. : 6,624,150 B2
APPLICATION NO. : 09/747777
DATED : September 23, 2003
INVENTOR(S) : Benjamin R. Yerxa et al.

It is certified that error appears in the above-identified patent and that said Letters Patent is hereby corrected as shown below:

At Claim 3, Column 27, lines 30–40, change formula from:

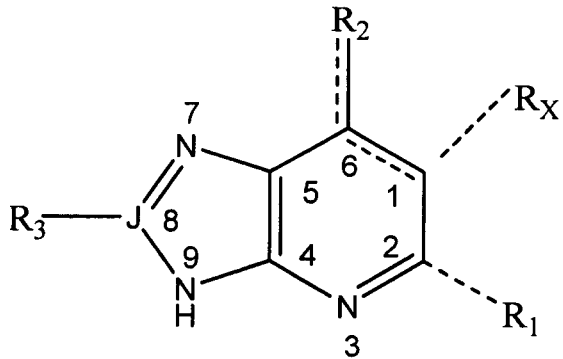

to:

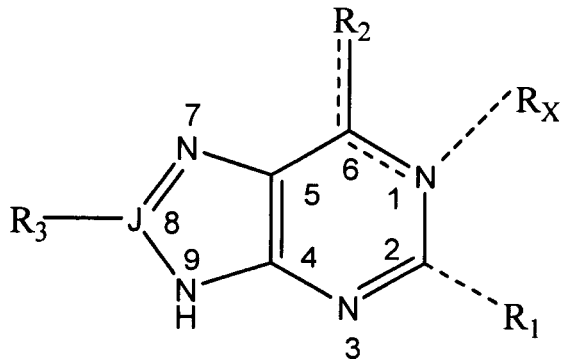

At Claim 4, Column 29, line 18, change "IP51" to --$IP_5I$--.
At Claim 5, Column 30, line 50, change "R6" to --$R_6$--.
At Claim 6, Column 31, line 60, change "R4" to --$R_4$--;
At Claim 6, Column 32, line 22, change "R6" to --$R_6$--.
At Claim 7, Column 32, line 63, change "R4" to --$R_4$--;
At Claim 7, Column 33, line 29, change "R4" to --$R_4$--;
At Claim 7, Column 33, line 34, change "R4," to --$R_4$,--;

UNITED STATES PATENT AND TRADEMARK OFFICE
CERTIFICATE OF CORRECTION

PATENT NO. : 6,624,150 B2
APPLICATION NO. : 09/747777
DATED : September 23, 2003
INVENTOR(S) : Benjamin R. Yerxa et al.

It is certified that error appears in the above-identified patent and that said Letters Patent is hereby corrected as shown below:

At Claim 7, Column 35, lines 54-64, change formula from:

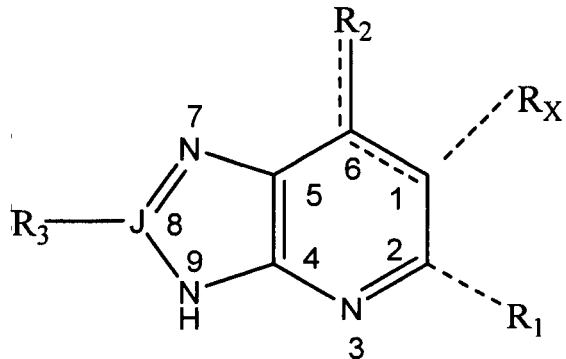

to:

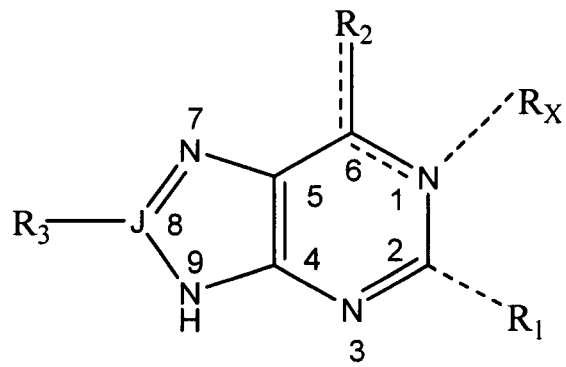

Signed and Sealed this

Seventh Day of November, 2006

JON W. DUDAS
*Director of the United States Patent and Trademark Office*